(12) United States Patent
Redinger et al.

(10) Patent No.: US 11,609,203 B2
(45) Date of Patent: Mar. 21, 2023

(54) SUPPRESSING THERMALLY INDUCED VOLTAGES FOR VERIFYING STRUCTURAL INTEGRITY OF MATERIALS

(71) Applicant: 3M INNOVATIVE PROPERTIES COMPANY, St. Paul, MN (US)

(72) Inventors: David H. Redinger, Afton, MN (US); Christopher R. Yungers, Saint Paul, MN (US); Jennifer F. Schumacher, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 17/303,867

(22) Filed: Jun. 9, 2021

(65) Prior Publication Data
US 2021/0293736 A1 Sep. 23, 2021

Related U.S. Application Data

(63) Continuation of application No. 16/461,464, filed as application No. PCT/US2017/061792 on Nov. 15, 2017, now Pat. No. 11,060,993.
(Continued)

(51) Int. Cl.
*G01N 27/20* (2006.01)
*G01N 33/38* (2006.01)

(52) U.S. Cl.
CPC ........... *G01N 27/20* (2013.01); *G01N 33/388* (2013.01)

(58) Field of Classification Search
CPC ...... G01N 27/20; G01N 27/61; G01N 27/045; G01N 27/041; G01N 27/02; G01N 33/38; G01B 5/28; G01B 7/06; G06F 19/00
See application file for complete search history.

(56) References Cited

U.S. PATENT DOCUMENTS 4,764,970 A 8/1988 Hayashi et al.
4,785,243 A 11/1988 Abramczyk et al.
(Continued)

FOREIGN PATENT DOCUMENTS

CN 101832970 A 9/2010
CN 205003121 U 1/2016
(Continued)

OTHER PUBLICATIONS

Anatychuk, L.I., "Procedure and Equipment for Measuring Parameters of Thermoelectric Generator Modules", Journal of Electronic Materials, vol. 40, No. 5, 2011, pp. 1292-1297.
(Continued)

*Primary Examiner* — Vinh P Nguyen
(74) *Attorney, Agent, or Firm* — Sriram Srinivasan

(57) ABSTRACT

The disclosure describes techniques for detecting a crack or defect in a material. The technique may include applying an electrical signal to a first electrode pair electrically coupled to the material. The technique also may include, while applying the electrical signal to the first electrode pair, determining a measured voltage between a second, different electrode pair. At least one electrode of the second, different electrode pair is electrically coupled to the material. The technique may further include determining a corrected measured voltage by suppressing a thermally induced voltage from the measured voltage and determining whether the material includes a crack or other defect based on the corrected measured voltage.

15 Claims, 5 Drawing Sheets

Related U.S. Application Data

(60) Provisional application No. 62/422,950, filed on Nov. 16, 2016.

(56) References Cited

U.S. PATENT DOCUMENTS

| | | | |
|---|---|---|---|
| 4,914,378 A | 4/1990 | Hayashi et al. | |
| 5,258,708 A | 11/1993 | Sadeghi et al. | |
| 5,969,532 A * | 10/1999 | Usui | G01N 27/205 324/693 |
| 6,150,809 A | 11/2000 | Tiernan et al. | |
| 6,210,972 B1 | 4/2001 | Williams et al. | |
| 6,218,846 B1 | 4/2001 | Ludwig et al. | |
| 6,288,528 B1 | 9/2001 | Goodstein et al. | |
| 6,476,624 B1 | 11/2002 | Chuman et al. | |
| 6,922,641 B2 * | 7/2005 | Batzinger | G01B 7/281 702/35 |
| 7,157,920 B2 * | 1/2007 | Barber | G01N 27/20 324/718 |
| 7,161,356 B1 | 1/2007 | Chien | |
| 7,180,302 B2 * | 2/2007 | Kelsey | F41H 5/0435 324/693 |
| 7,443,177 B1 | 10/2008 | Bowler | |
| 7,519,487 B2 * | 4/2009 | Saguy | G01N 27/20 73/799 |
| 7,596,470 B2 | 9/2009 | Kim | |
| 7,705,589 B2 | 4/2010 | Kim et al. | |
| 8,327,306 B2 | 12/2012 | Oh et al. | |
| 8,552,752 B2 | 10/2013 | Qiu | |
| 8,624,401 B2 | 1/2014 | Ishikawa | |
| 8,816,705 B2 | 8/2014 | Espejord | |
| 9,037,430 B1 | 5/2015 | Wiggins et al. | |
| 11,016,047 B2 * | 5/2021 | Redinger | G01N 27/20 |
| 2002/0024346 A1 | 2/2002 | Ikuta et al. | |
| 2003/0184321 A1 | 10/2003 | Hands | |
| 2004/0021461 A1 | 2/2004 | Goldfine et al. | |
| 2004/0241890 A1 | 12/2004 | Steele et al. | |
| 2005/0251062 A1 | 11/2005 | Choi et al. | |
| 2006/0283262 A1 | 12/2006 | Smits et al. | |
| 2008/0001608 A1 | 1/2008 | Saulnier et al. | |
| 2008/0191706 A1 | 8/2008 | Burnett et al. | |
| 2009/0121727 A1 | 5/2009 | Lynch et al. | |
| 2009/0192730 A1 | 7/2009 | Tada | |
| 2009/0202387 A1 | 8/2009 | Dlugos, Jr. et al. | |
| 2011/0060536 A1 | 3/2011 | Feng | |
| 2012/0013483 A1 | 1/2012 | Jung et al. | |
| 2012/0024346 A1 | 2/2012 | Bystrom et al. | |
| 2012/0153740 A1 | 6/2012 | Soar | |
| 2012/0177177 A1 | 7/2012 | Masters | |
| 2012/0235693 A1 | 9/2012 | Feng | |
| 2013/0307566 A1 | 11/2013 | Malone et al. | |
| 2014/0062521 A1 | 3/2014 | Yamada | |
| 2014/0152336 A1 | 6/2014 | Sasaki et al. | |
| 2014/0354307 A1 | 12/2014 | Clarke et al. | |
| 2015/0095000 A1 | 4/2015 | Patil et al. | |
| 2015/0204701 A1 | 7/2015 | Klicpea | |
| 2015/0308980 A1 | 10/2015 | Bittar et al. | |
| 2016/0163607 A1 | 6/2016 | Oh et al. | |
| 2017/0167927 A1 | 6/2017 | Carkner | |

FOREIGN PATENT DOCUMENTS

| | | |
|---|---|---|
| JP | S56-012544 | 2/1981 |
| JP | S62-047544 | 3/1987 |
| JP | H03-056848 A | 12/1991 |
| JP | H05-288706 A | 2/1993 |
| WO | WO 89/012833 A1 | 12/1989 |
| WO | WO 2007/075243 A1 | 7/2007 |

OTHER PUBLICATIONS

Aselage, T.L., et. al., "Large Enhancement of Boron Carbides' Seebeck Coefficients through Vibrational Softening" Physical Review Letters, vol. 81, No. 11, 1998, pp. 2316-2319.

Hartov, Alex, et al. "Using voltage sources as current drivers for electrical impedance tomography", Measurement Science and Technology, vol. 13, 2002, pp. 1425-1430.

International Search Report for PCT International Application No. PCT/US2017/061792, dated Jan. 29, 2018, 2 pages.

Lazarovitch, R., et al., "Experimental crack identification using electrical impedance tomography", NDT&E International, vol. 35, No. 5, pp. 301-316, Jul. 1, 2002.

Paraskevopoulous, I., "Solar Soldier: Virtual Reality Simulations and Guidelines for the Integration of Photovoltaic Technology on the Modern Infantry Soldier", School of Engineering and Design, Brunel University, U.K. 141-154.

Ruan, Tao, "Development of an Automated Impedance Tomography System and Its Implementation in Cementitious Materials", Clemson University—TigerPrints, All Dissertations Paper 1756, 2016, pp. 25-49.

Sauliner, Gary J., et al. "A high-precision voltage source for ETI", Physiological Measurement, Institute of Physics Publishing, Bristol, GB, vol. 27, No. 5, May 1, 2006, pp. S221-S236 (XP020105771).

Steinitz, Avital A. "Optimal Camera Placement." 2012 Thesis. (http://www.eecs.berkeley.edu/Pubs/TechRpts/2012/EECS-2012-69.pdf).

Valiant, Leslie G. "The Complexity of Enumeration and Reliability Problems," *SIAM Journal on Computing*, vol. 8, Issue 3, 1979, pp. 410-421.

Zaoui, Abdelhalim "Inverse Problem in Nondestructive Testing Using Arrayed Eddy Current Sensors", Sensors, 2010, vol. 10, p. 8696-8704.

* cited by examiner

SUPPRESSING THERMALLY INDUCED VOLTAGES FOR VERIFYING STRUCTURAL INTEGRITY OF MATERIALS

CROSS REFERENCE TO RELATED APPLICATIONS

This application is a Continuation of U.S. application Ser. No. 16/461,464 filed 16 May 2019, now, U.S. Pat. No. 11,060,993, which is a U.S. 371 application based on International Application No. PCT/US2017/061792 filed on 15 Nov. 2017, which claims the benefit of Provisional U.S. Patent Application No. 62/422,950 filed 16 Nov. 2016, the entire disclosure of each of which is incorporated herein by reference.

TECHNICAL FIELD

The disclosure relates to techniques for verifying structural integrity of conductive or semiconductive materials.

BACKGROUND

Many materials are useful when their mechanical properties remain intact, but less useful when damaged, such as when cracked. Thus, detection whether these materials are damaged is important. As one example, ceramic body plating is used to protect soldiers, police officers, and other security personnel from projectiles. Ceramic body plating may be useful when undamaged, but may be replaced after being damaged, e.g., after cracking.

X-ray scanning, including X-ray radiography and X-ray computed tomography (CT scanning) may be used to detect cracks or other defects in materials. However, such techniques may utilize large and heavy scanners, which may not be easily portable. Further, X-ray scanning and X-ray CT scanning may be relatively expensive, relatively slow, or both.

SUMMARY

In general, this disclosure describes systems and techniques for verifying structural integrity of a material. The techniques may include suppressing a thermally induced voltage in the material from a measured voltage to arrive at a corrected measured voltage. For example, an electrical signal source may apply a first electrical signal having a first polarity to the material via a pair of drive electrodes and a first resulting voltage may be determined (e.g., measured or determined from another measured electrical parameter) via a pair of measurement electrodes. One or both electrodes of the pair of measurement electrodes is electrically coupled to the material. In examples in which both electrodes of the pair of measurement electrodes are electrically coupled to the material, the first resulting voltage is the voltage difference between the first and second measurement electrodes electrically coupled to the material. In examples in which one electrode of the pair of measurement electrodes is electrically coupled to the material, the other electrode of the pair of measurement electrodes may be at a reference voltage, such as ground. In such examples, the first resulting voltage is the voltage difference between the first measurement electrode electrically coupled to the material and the second measurement electrode at the reference voltage. The electrical signal source also may apply a second electrical signal having a second, opposite polarity to the material via the pair of drive electrodes and a second resulting voltage may be determined (e.g., measured or determined from another measured electrical parameter) via the pair of measurement electrodes. By subtracting the first resulting voltage from the second resulting voltage, an effect of any thermally induced voltage may be reduced.

As another example, the pair of measurement electrodes may be used to determine the thermally induced voltage when the electrical signal source is not applying an electrical signal to the pair of drive electrodes and the pair of measurement electrodes. The thermally induced voltage then may be subtracted from a measurement voltage associated with the same pair of measurement electrodes. By suppressing the thermally induced voltage from the measurement voltage, the techniques described herein may facilitate more accurate determination of whether the material includes a crack or other defect.

In some examples, the disclosure describes a method that includes applying an electrical signal to a first electrode pair electrically coupled to the material. The method also may include, while applying the electrical signal to the first electrode pair, determining a measured voltage between a second, different electrode pair. At least one electrode of the second, different electrode pair is electrically coupled to the material. The method may further include determining a corrected measured voltage by suppressing a thermally induced voltage from the measured voltage and determining whether the material includes a crack or other defect based on the corrected measured voltage.

In some examples, the disclosure describes a method that includes, for each respective pair of drive electrodes of a plurality of respective pairs of drive electrodes electrically coupled to the material, applying an electrical signal to the respective pair of drive electrodes. The method also may include, for each respective pair of drive electrodes, determining a respective measured voltage between each respective pair of measurement electrodes of a plurality of pairs of measurement electrodes while applying the electrical signal to the respective pair of drive electrodes. At least one electrode of each respective pair of measurement electrodes is electrically coupled to the material. The method further may include determining a respective corrected measured voltage for each respective pair of measurement electrodes by suppressing a respective thermally induced voltage from the respective measured voltage. Additionally, the method may include determining whether the material includes a crack or other defect based on the respective corrected measured voltages.

In some examples, the disclosure describes a system that includes a set of N electrodes electrically coupled to a material, an electrical signal source, and a computing device. The computing device may be configured to cause the electrical signal source to apply an electrical signal to a first electrode pair from the set of N electrodes. The computing device also may be configured to, while electrical signal source is applying the electrical signal to the first electrode pair, determine a measured voltage between a second, different electrode pair. At least one electrode of the second, different electrode pair is from the set of N electrodes. The computing device further may be configured to determine a corrected measured voltage by suppressing a thermally induced voltage from the measured voltage and determine whether the material includes a crack or other defect based on the corrected measured voltage.

The techniques described herein may provide one or more advantages. For example, suppressing the thermally induced voltage from the measurement voltage may result in improved accuracy and sensitivity for detecting cracks or other defects in a material compared to a technique that does not suppress thermally induced voltage from the measurement voltage. As another example, a four-point voltage measurement system may offer improved portability and cost compared to an X-ray radiography or X-ray computed tomography system, while offering sufficient accuracy and detail to enable detection of cracks or other defects in a material being used in the field.

The details of one or more examples are set forth in the accompanying drawings and the description below. Other features, objects, and advantages will be apparent from the description and drawings, and from the claims.

DETAILED DESCRIPTION

Figure 1:
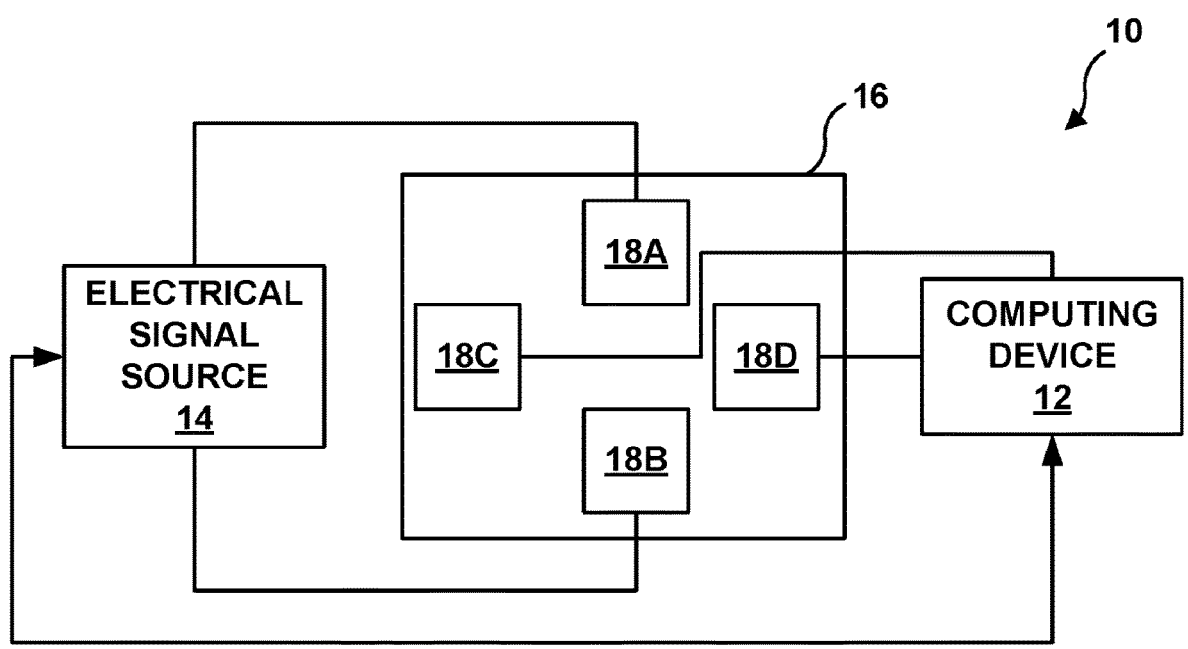
FIG. 1 is a conceptual and schematic diagram block illustrating an example system for determining whether a material includes a crack or other defect by measuring a voltage in the material and suppressing thermally induced voltage from the measured voltage.

The disclosure describes systems and techniques for verifying structural integrity of a material. The techniques may suppress or substantially remove thermally induced voltage from a measured voltage to determine a corrected measured voltage. Thermally induced voltage may arise from a thermoelectric effect, such as the Seebeck Effect, the Peltier Effect, the Thomson Effect, or combinations thereof. The techniques described herein may utilize the corrected measured voltage to determine whether the material includes a crack or other defect.

The thermally induced voltage may be suppressed from the measured voltage using one or more of a variety of techniques. In some example techniques, an electrical signal source may apply a first electrical signal having a first polarity to the material via a pair of drive electrodes and a first resulting voltage may be determined (e.g., measured or determined from another measured electrical parameter) via a pair of measurement electrodes. The electrical signal source also may apply a second electrical signal having a second, opposite polarity to the material via the pair of drive electrodes and a second resulting voltage may be determined (e.g., measured or determined from another measured electrical parameter) via the pair of measurement electrodes. By subtracting the first resulting voltage from the second resulting voltage, an effect of any thermally induced voltage may be reduced.

As another example, the pair of measurement electrodes may be used to determine the thermally induced voltage when the electrical signal source is not applying an electrical signal to the pair of drive electrodes and the pair of measurement electrodes. The thermally induced voltage then may be subtracted from a measurement voltage associated with the same pair of measurement electrodes.

Regardless of the technique by which the thermally induced voltage is determined and suppressed or substantially removed from the measured voltage, suppressing the thermally induced voltage from the measurement voltage may facilitate more accurate determination of whether the material includes a crack or other defect. In some examples, thermally induced voltage internal to the material may be comparable in magnitude to the measured voltage. Hence, if the thermally induced voltage is not suppressed from the measured voltage, thermally induced voltage may be a significant source of noise in determining whether the material includes a crack or other defect.

For example, the material may include a semiconductive ceramic material, such as boron carbide or silicon carbide. Noise due to thermally induced voltage may be most significant when the semiconductive materials are hot. When the semiconducting material is hot, the electrical conductivity of the sample is higher and hence the measured voltage is smaller. Thus the magnitude of the noise is higher relative to the relatively smaller measured voltage. For example, boron carbide has a fairly high Seebeck Coefficient, in the range of 200-300 micro-V/K. This is about an order of magnitude larger than the Seebeck Coefficient of silicon carbide. Further, boron carbide has a higher conductivity than silicon carbide. In practice this noise attributable to thermally induced voltage may be about 2 orders of magnitude more significant in boron carbide material than silicon carbide material. Hence, it may be important for accurate voltage measurements to account for a suppress thermally induced voltage from the measured voltage.

Once the thermally induced voltage has been suppressed from the measured voltage to determined a corrected measured voltage, the corrected measured voltage may be compared to a control voltage or a predetermined threshold voltage to determine whether the material is damaged or intact. In some examples, the control voltage may be determined for the same material via the same pair of measurement electrodes when the material is known to be intact (undamaged), the control voltage may be determined using a model of the material in an intact (undamaged) state, or the control voltage may be determined as an average (e.g., mean) of a plurality of similar materials (e.g., in geometry and composition) that are known to be intact (undamaged). In some examples, the predetermined threshold voltage may be selected so that a voltage below the threshold voltage value is indicative of a crack or other defect and a voltage above the threshold voltage value is not indicative of a crack or other defect.

In some examples, suppressing the thermally induced voltage from the measured voltage may be combined with a four-point voltage measurement. A four-point voltage measurement may provide advantages compared to two-point voltage measurements and other techniques for verifying structural integrity. A two-point voltage measurement may be affected not only by electrical property variations in the material under test, but also in any electrical connections between the measurement apparatus and the material, such as within electrical leads, in electrical contacts between the leads and the material, or the like. In some examples, variations in electrical properties of these components may complicate measurement of voltage across the material under test, as these electrical properties may vary differently (in magnitude, direction, or both) than the electrical properties of the material under test. In some examples, one or more of these electrical properties may actually vary to a greater extent than the change in electrical properties, such as resistivity, conductivity, or other related electrical properties, in the material due to a crack, which may obscure the change in electrical properties in the material due to a crack. By using a four-point voltage measurement, the contributions of the electrical leads coupling the pair of measurement electrodes to the measurement device and any contact-related error sources (e.g., contact resistance) between the pair of measurement electrodes and the material may be reduced or substantially eliminated, as little current flows to the measurement device. Hence, by utilizing both a four-point voltage measurement and suppressing thermally induced voltage from the measured voltage may reduce or substantially eliminate temperature effects in the material and the measurement system when utilizing the measured voltage to determine whether the material includes a crack or other defect.

Other techniques also may be used to detect cracks in a material. For example, X-ray radiography or X-ray computed tomography (CT) may be used to detect cracks in a material. However, X-ray radiography and X-ray CT utilize relatively large, relatively expensive equipment to perform the crack detection. This may prevent X-ray radiography and X-ray CT from being portable, such as being used to test materials in the environments in which they are used. Moreover, X-ray radiography and X-ray CT may be relatively time consuming.

In contrast, a voltage measurement utilizes relatively smaller, relatively less expensive equipment. As such, the equipment may enable portable crack detection systems, which may be used to detect cracks in materials in situ rather than requiring suppressing the materials to be tested to the testing equipment.

FIG. 1 is conceptual and schematic diagram block illustrating an example system 10 for determining presence of a crack or other defect in a material 16 by measuring a voltage in the material and suppressing thermally induced voltage from the measured voltage. The system 10 of FIG. 1 includes a computing device 12, an electrical signal source 14, and a plurality of electrodes 18A-18D (collectively, "electrodes 18"). Electrodes 18 are electrically coupled to material 16, which, in the example of FIG. 1, is being tested using a four-point voltage measurement.

Material 16 may be any material for which detection of a potential crack or other defect is desired. In some examples, material 16 may be an electrically conductive or an electrically semiconductive material. For example, material 16 may include a metal, an alloy, a metalloid, a semiconductor, an electrically conductive or semiconductive ceramic, or the like. In some examples, material 16 may include a ceramic such as boron carbide ($B_4C$), silicon carbide (SiC), alumina ($Al_2O_3$), composites thereof, or the like.

Material 16 may be used in any one of a wide variety of applications. For example, material 16 may be a ceramic that has relatively high hardness, a relatively high Young's modulus, a relatively high tensile strength, and may be used in ceramic armor plating. Ceramic armor plating may be used in body armor for military and police personnel, vehicle armor, or the like. Example materials for ceramic armor plating include boron carbide ($B_4C$), silicon carbide (SiC), alumina ($Al_2O_3$), composites thereof, or the like.

Material 16 may define any geometry, and the geometry of material 16 may be based at least in part on the intended use for material 16. For example, ceramic armor plating may have a geometry defined by the surface that the armor plating will be applied to. Example geometries for material 16 include, but are not limited to, polygonal solids, such as rectangular solids or solids with more sides.

Electrical signal source 14 may include any device configured to output an electrical signal to electrodes 18. The electrical signal may include a direct current (DC) signal or an alternating current (AC) signal. In some examples, electrical signal source 14 may output a current signal; in other examples, electrical signal source 14 may output a voltage signal. Electrical signal source 14 may include a power source, such as a battery, a capacitor, a supercapacitor, a transformer electrically connected to a mains voltage, or the like. In some examples, in addition to the power source, electrical signal source 14 may include analog or digital circuitry configured to receive the electrical signal from the power source and modify the electrical signal into a format suitable for output to electrodes 18.

Electrodes 18 include a plurality of electrodes electrically coupled to material 16. In some examples, as shown in FIG. 1, electrodes 18 may include a pair of drive electrodes 18A and 18B each electrically coupled to electrical signal source 14, e.g., by a respective lead wire, and a pair of measurement electrodes 18C and 18D each electrically connected to computing device 12, e.g., by a respective lead wire. Each of electrodes 18 may be electrically connected to material 16 using any suitable type of electrical connection, including, for example, an electrically conductive adhesive, an electrically conductive solder, embedding electrodes 18 in material 16, or the like.

In some examples, rather than both measurement electrodes 18C and 18D being electrically coupled to material 16, only one of the measurement electrodes (e.g., measurement electrode 18C) of the pair of measurement electrodes is electrically coupled to the material. The other measurement electrode of the pair of measurement electrodes may be at a reference voltage, such as ground or a selected offset voltage. In such examples, the determined voltage is the voltage difference between the first measurement electrode electrically coupled to the material and the second measurement electrode at the reference voltage.

In some examples, electrodes 18 may include more than one pair of drive electrodes, more than one pair of measurement electrodes, or both. In some examples, as described below with respect to FIG. 3, electrodes 18 may include a plurality of electrodes connected to a switch network, which allows any electrode of the plurality of electrodes to be selectively coupled to electrical signal source 14 or computing device 12.

Electrodes 18 may be attached to any surface of material 16. The surface to which electrodes 18 are attached may affect the direction in which the electrical field extends and current flows within material 16. Cracks or other defects may affect the magnitude of the voltage more significantly when the electrical field and current flow extends across a plane of the crack (e.g., normal to a surface of the crack). As such, in some examples, the likely locations of cracks or other defects and the likely orientation of cracks or other defects within material 16 may be predicted based on the use for material 16. In some of these examples, electrodes 18 may then be attached to material 16 so that the electrical field and current flow within material 16 extends substantially normal to a predicted orientation of the crack or other defect.

In some examples, rather than predicting a location of the crack or other defect within material 16 and placing electrodes 18 based on the prediction, electrodes 18 may be attached to more than one surface of material 16. For example, if material 16 is in the shape of a cube, electrodes 18 may be attached to three orthogonal surfaces of the cube. By attaching a respective electrode of electrodes 18 to three orthogonal surfaces, the electrical field and current flow may be caused to extend in one of three orthogonal directions depending on the electrodes 18 through which the electrical signal is applied. This may increase a likelihood that induced the electrical field and current flow will extend within material 16 normal to the plane of any crack in material 16. Other examples are possible for other shapes.

Computing device 12 is configured to control operation of system 10, including electrical signal source 14. Computing device 12 may include any of a wide range of devices, including, but not limited to, computer servers, desktop computers, notebook (i.e., laptop) computers, tablet computers, and the like. In some examples, computing device 12 may include a processor. The processor may include one or more microprocessors, digital signal processors (DSP), application specific integrated circuits (ASIC), field programmable gate arrays (FPGA), or other digital logic circuitry. In some examples, computing device 12 may include an analog-to-digital converter (ADC), or system 10 may include an ADC separate from computing device 12. In examples in which the ADC is separate from computing device 12, the ADC may be electrically coupled between measurement electrode 18C and computing device 12 and between measurement electrode 18D and computing device 12. The ADC may measure the voltage across measurement electrodes 18C and 18D, e.g., under control of computing device 12.

Computing device 12 is electrically coupled to the pair of measurement electrodes 18C and 18D, and communicatively coupled to electrical signal source 14. Computing device 12 may be configured to cause electrical signal source 14 to apply an electrical signal (e.g., a voltage signal or current signal) to the pair of drive electrodes 18A and 18B. Computing device 12 also may be configured to determine a voltage across the pair of measurement electrodes 18C and 18D in response to the electrical signal, regardless of whether one or both of measurement electrodes 18C and 18D are electrically coupled to material 16. In some examples, computing device 12 includes an ADC that measures the voltage across the pair of measurement electrodes 18C and 18D. In other examples, computing device 12 controls an external ADC to measure the voltage across the pair of measurement electrodes 18C and 18D. In other examples, computing device 12 may measure or control another device to measure another electrical parameter (e.g., current) and may determine the voltage based on the measured electrical parameter.

By using a four-point voltage measurement, the contributions of the electrical leads coupling the pair of measurement electrodes 18C and 18D to computing device 12 and any contact resistance between measurement electrodes 18C and 18D and material 16 may be reduced or substantially eliminated, as little current flows to computing device 12. Hence, a four-point voltage measurement may facilitate measurement of voltages in material 16 and detection of cracks due to changes in electrical properties, such as resistivity, conductivity, or other related electrical properties.

In some examples, to determine whether material 16 includes a crack or other defect, computing device 12 may determine a control voltage. The control voltage may be based on material 16, a model, or an average of a plurality of materials that are similar to or substantially the same as material 16. For example, computing device 12 or another similar computing device may determine the control voltage at a time at which material 16 is manufactured, or a time at which an independent measurement (e.g., X-ray radiology or X-ray CT scan) may be used to verify that material 16 is intact, undamaged, or does not include a crack. Computing device 12 or the other similar computing device may determine by control voltage by applying the electrical signal to the pair of drive electrodes 18A and 18B and determining the voltage across the measurement electrodes 18C and 18D.

In other examples, the control voltage may be determined using a model of the material in an intact (undamaged) state. For example, computing device 12 may execute the model of material 16 and determine the control voltage based on the model. In some examples, the model may include a physics-based model of the electrical properties of material 16, such as the physics-based model described below. In some other examples, the control voltage may be determined as an average (e.g., mean) of a plurality of similar materials (e.g., in geometry and composition) that are known to be intact (undamaged). This control voltage may be stored (e.g., in a memory device associated with computing device 12) for later use.

At a later time, system 10 then may be used to determine a measurement voltage using the four-point measurement test described above. For example, computing device 12 may control electrical signal source 14 to apply an electrical signal (e.g., a voltage signal or a current signal) to a pair of drive electrodes 18A and 18B and measure a voltage across the pair of measurement electrodes 18C and 18D or determine the voltage across the pair of measurement electrodes 18C and 18D based on another electrical parameter measured across the pair of measurement electrodes 18C and 18D (e.g., current).

Computing device 12 also may be configured to suppress a thermally induced voltage from the measured voltage. As described above, depending on the composition of material 16, the temperature of material 16, and the presence of any thermal gradients within material 16, in some examples, thermally induced voltage in material 16 may be a significant source of noise when determining the measured voltage. Thus, suppressing the thermally induced voltage from the measured voltage may improve allow computing device 12 to make a more accurate determination of whether material 16 includes a crack or other defect than in examples in which the thermally induced voltage is not suppressed from the measured voltage.

In some examples, in order to suppress the thermally induced voltage from the measured voltage, computing device 12 may determine the thermally induced voltage between the pair of measurement electrodes 18C and 18D. For example, computing device 12 may determine a voltage between pair of measurement electrodes 18C and 18D when electrical signal source 14 is not applying the electrical signal to the pair of drive electrodes 18A and 18B and is not applying the electrical signal to the pair of measurement electrodes 18C and 18D. Any voltage in material 16 detected between pair of measurement electrodes 18C and 18D when no electrical signal is being applied to material may be thermally induced voltage. Computing device 12 then may suppress the thermally induced voltage from the measured voltage by subtracting the determined thermally induced voltage from the determined measured voltage to arrive at a corrected measured voltage.

In some examples, rather than determining the thermally induced voltage between the pair of measurement electrodes 18C and 18D, computing device 12 may suppress the thermally induced voltage without first determining it. For example, computing device 12 may control electrical signal source 14 to apply a first electrical signal (e.g., a first DC current signal) with a first polarity to the pair of drive electrodes 18A and 18B, and may determine a first measured voltage between the pair of measurement electrodes 18C and 18D while electrical signal source 14 is applying the first electrical signal to the pair of drive electrodes 18A and 18B. Computing device 12 then may control electrical signal source 14 to apply a second electrical signal (e.g., a second DC current signal) with a second, opposite polarity to the pair of drive electrodes 18A and 18B. Computing device 12 may determine a second measured voltage between the pair of measurement electrodes 18C and 18D while electrical signal source 14 is applying the second electrical signal to the pair of drive electrodes 18A and 18B. Aside from having opposite polarities, the first and second electrical signals may be substantially the same (e.g., in magnitude, duration, frequency, and the like).

Because the first and second electrical signals have opposite polarities, the measured voltages will have different signs. However, as the thermally induced voltage is due to temperature differences in material 16, which are the same during the first and second measurements, subtracting the first measured voltage from the second measured voltage (or vice versa) will result in reducing an effect of the thermally induced voltage from the measured voltages, along with doubling of the magnitude of the measured voltage. In this way, computing device 12 may suppress the thermally induced voltage from the measured voltage without directly determining the thermally induced voltage. In some examples, computing device 12 may divide the result of subtracting the first measured voltage from the second measured voltage by two to determine the corrected measured voltage; in other examples, computing device 12 may utilize the result of subtracting the first measured voltage from the second measured voltage as the corrected measured voltage.

Once computing device 12 has determined the corrected measured voltage, computing device 12 may determine whether material 16 includes a crack or other defect based on the corrected measured voltage, for example, by comparing the measured voltage to the control voltage. As one example, computing device 12 may determine a difference between a magnitude of the measurement voltage and a magnitude of the control voltage. Computing device 12 then may compare this difference to a threshold voltage value, and may determine that material 16 includes a crack or other defect in response to the difference being greater than the threshold voltage value. In some examples in which computing device 12 determines the control voltage by measuring a voltage when material 16 is known to be intact, computing device 12 may suppress thermally induced voltage from the control voltage using techniques similar or substantially the same as those described above with reference to the measured voltage.

As another example, computing device 12 may compare the measurement voltage to a threshold voltage value, and may determine that material 16 includes a crack or other defect in response to the measurement voltage being less than the threshold voltage value.

In this way, suppressing thermally induced voltage from a measured voltage, alone or in combination with a four-point voltage measurement, may offer improved accuracy and sensitivity for detecting cracks or other defects in material 16. Additionally, a four-point voltage measurement system 10 may offer improved portability and cost compared to an X-ray radiography or X-ray computed tomography system, while offering sufficient accuracy and detail to enable detection of cracks or other defects in material 16 while material 16 is being used in the field.

Figure 2:
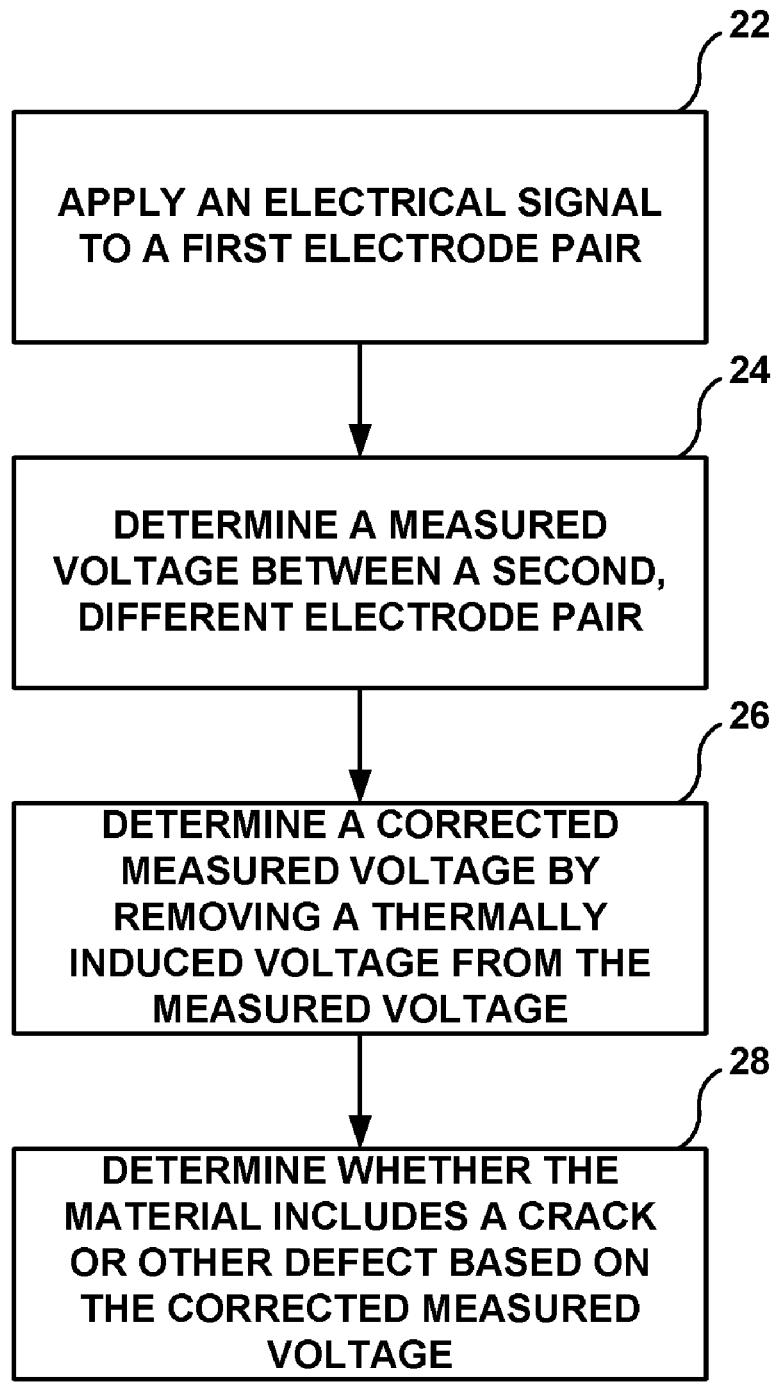
FIG. 2 is a flow diagram illustrating an example technique for determining whether a material includes a crack or other defect by measuring a voltage in the material and suppressing thermally induced voltage from the measured voltage.

FIG. 2 is flow diagram illustrating an example technique for determining presence of a crack or other defect in a material by measuring a voltage in the material and suppressing thermally induced voltage from the measured voltage. The technique of FIG. 2 will be described with reference to system 10 and computing device 12 of FIG. 1 for clarity. However, it will be appreciated that the technique of FIG. 2 may be performed by other systems and computing devices, and that system 10 and computing device 12 may be used to perform other techniques.

The technique of FIG. 2 includes applying an electrical signal to a first electrode pair, such as the pair of drive electrodes 18A and 18B, electrically coupled to a material 16 (22). For example, computing device 12 may control electrical signal source 14 to generate a predetermined electrical signal. The predetermined electrical signal may include, for example, a DC signal, and may be a current or a voltage. In some examples, the type of electrical signal may depend on the composition of material 16. For example, a DC signal may be used to measure a voltage of an electrically conductive or electrically semiconductive material, while an AC signal may be used to measure a voltage of an electrically conductive material, an electrically semiconductive material, or a dielectric material. Computing device 12 also may control electrical signal source 14 to generate the predetermined electrical signal with a selected amplitude, duration, frequency, and other signal characteristics.

The technique of FIG. 2 also includes, while applying the electrical signal to the first electrode pair, such as the pair of drive electrodes 18A and 18B, determining voltage between a second, different electrode pair, such as the pair of measurement electrodes 18C and 18D, electrically coupled to material 16 (24). For example, computing device 12 may measure or cause another device (e.g., an external ADC) to measure a voltage across the pair of measurement electrodes 18C and 18D or determine the voltage across the pair of measurement electrodes 18C and 18D based on another electrical parameter measured across the pair of measurement electrodes 18C and 18D (e.g., current).

The technique of FIG. 2 further includes determining a corrected measured voltage by suppressing a thermally induced voltage from the measured voltage (26). In some examples, in order to suppress the thermally induced voltage from the measured voltage (26), computing device 12 may determine the thermally induced voltage between the pair of measurement electrodes 18C and 18D. For example, computing device 12 may determine a voltage between the pair of measurement electrodes 18C and 18D when electrical signal source 14 is not applying the electrical signal to the pair of drive electrodes 18A and 18B and is not applying the electrical signal to the pair of measurement electrodes 18C and 18D. Any voltage in material 16 detected between pair of measurement electrodes 18C and 18D when no electrical signal is being applied to material may be thermally induced voltage. Computing device 12 then may suppress the thermally induced voltage from the measured voltage (26) by subtracting the determined thermally induced voltage from the determined measured voltage to arrive at the corrected measured voltage.

In some examples, rather than determining the thermally induced voltage between the pair of measurement electrodes 18C and 18D, computing device 12 may suppress the thermally induced voltage without first determining it. For example, computing device 12 may control electrical signal source 14 to apply a first electrical signal (e.g., a first DC current signal) with a first polarity to the pair of drive electrodes 18A and 18B, and may determine a first measured voltage between the pair of measurement electrodes 18C and 18D while electrical signal source 14 is applying the first electrical signal to the pair of drive electrodes 18A and 18B. Computing device 12 then may control electrical signal source 14 to apply a second electrical signal (e.g., a second DC current signal) with a second, opposite polarity to the pair of drive electrodes 18A and 18B. Computing device 12 may determine a second measured voltage between the pair of measurement electrodes 18C and 18D while electrical signal source 14 is applying the second electrical signal to the pair of drive electrodes 18A and 18B. Aside from having opposite polarities, the first and second electrical signals may be substantially the same (e.g., in magnitude, duration, frequency, and the like).

Because the first and second electrical signals have opposite polarities, the measured voltages, in the absence of thermoelectric voltage, would have different signs. However, as the thermally induced voltage is due to temperature differences in material 16, which are the same during the first and second measurements, subtracting the first measured voltage from the second measured voltage (or vice versa) will result in reducing an effect of the contribution of the thermally induced voltage from the measured voltages, along with doubling of the magnitude of the measured voltage. In this way, computing device 12 may suppress the thermally induced voltage from the measured voltage (26) without directly determining the thermally induced voltage. In some examples, computing device 12 may divide the result of subtracting the first measured voltage from the second measured voltage by two to determine the corrected measured voltage; in other examples, computing device 12 may utilize the result of subtracting the first measured voltage from the second measured voltage as the corrected measured voltage.

The technique of FIG. 2 further includes determining whether a crack or other defect is present in material 16 based on the corrected measured voltage (28). For example, computing device 12 may compare the corrected measured voltage to a control voltage. In some examples, the control voltage may have been measured by system 10 or another similar system by applying a similar electrical signal to the pair of drive electrodes 18A and 18B and measuring the voltage across the pair of measurement electrodes 18C and 18D. In some examples, computing device 12 may have suppressed thermally induced voltage from the control voltage in a manner similar to those described above with reference to the measured voltage. However, the control voltage may have been measured at a time when material 16 was known to be defect-free. In some examples, computing device 12 may have suppressed thermally induced voltage from the control voltage in a manner similar to those described above with reference to the measured voltage. In other examples, the control voltage may be determined, by computing device 12 or another device, using a model of the material in an intact (undamaged) state, or the control voltage may be determined as an average (e.g., mean) of a plurality of similar materials (e.g., in geometry and composition) that are known to be intact (undamaged).

In some examples, computing device 12 may determine whether material 16 includes a crack or other defect based on the corrected measured voltage (26) by first determining a difference between a magnitude of the corrected measured voltage to a magnitude of the control voltage. For example, computing device 12 may subtract the magnitude of the control voltage from the magnitude of the corrected measured voltage to determine the difference. Computing device 12 then may compare this difference to a threshold voltage value. The threshold voltage value may be selected so that a voltage difference above the threshold voltage value is meaningful (e.g., indicative of a crack or other defect) and a voltage difference below the threshold voltage value is not meaningful (e.g., is not indicative of a crack or other defect). In some examples, the threshold voltage value may be selected to be a voltage value that is slightly greater than a noise floor of the measurement, such that any voltage difference that exceeds the noise floor is determined by computing device 12 to be indicative of a crack or other defect. In this way, in some examples, computing device 12 may compare the difference between the corrected measured voltage and the control voltage to a threshold voltage value, and may determine that material 16 includes a crack or other defect in response to the difference being greater than the threshold voltage value.

As another example, computing device 12 may compare the corrected measured voltage to a threshold voltage value, and may determine that material 16 includes a crack or other defect in response to the corrected measured voltage being greater than the threshold voltage value. In some examples, the threshold voltage may be selected so that a voltage above the threshold voltage value is indicative of a crack or other defect and a voltage below the threshold voltage value is not indicative of a crack or other defect.

In some examples, rather than directly utilizing the measured voltages to determine whether material 16 includes a crack or other defect based on the corrected measured voltage (26), computing device 12 may derive a parameter from the voltage, then utilize the derived parameter to determine whether material 16 includes a crack or other defect. As the derived parameter is derived based on the corrected measured voltages, such a determination is still based on the corrected measured voltage. For example, computing device 12 may determine a resistance based on an applied current and the corrected measured voltage, and may determine whether material 16 includes a crack or other defect based on the derived resistance.

In some examples, rather than including a single pair of drive electrodes 18A and 18B and a single pair of measurement electrodes 18C and 18D, a system may include a plurality of electrodes electrically coupled to a material to be tested. By including more electrodes, the system may utilize more data for determining whether the material includes a crack or other defect, which may provide more accuracy or precision, and, in some examples, may allow the system to estimate a position of the crack or other defect within the material.

Figure 3:
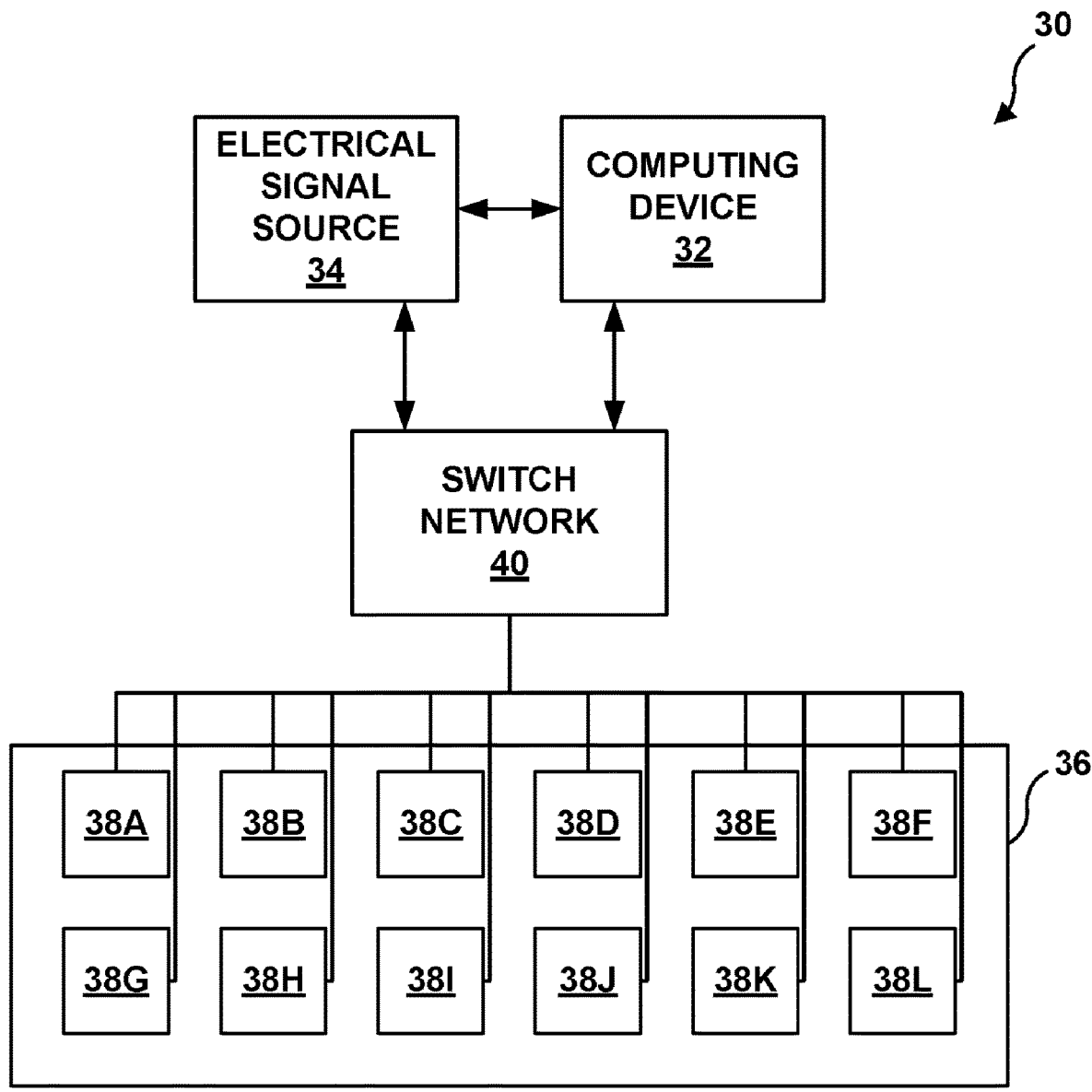
FIG. 3 is a conceptual and schematic block diagram illustrating an example system for determining whether a material includes a crack or other defect by measuring a voltage in the material and suppressing thermally induced voltage from the measured voltage.

For example, FIG. 3 is conceptual and schematic block diagram illustrating an example system 30 for determining presence of a crack or other defect in a material 36 using a four-point voltage measurement. System 30 of FIG. 3 includes a computing device 32, an electrical signal source 34, a plurality of electrodes 38A-38L (collectively, "electrodes 38"), and a switch network 40. Plurality of electrodes 38 are electrically coupled to material 36, which is being tested using a four-point voltage measurement.

Material 36 may include any material for which detection of a potential crack or other defect is desired. For example, material 36 may include any of the materials described above with reference to material 16 of FIG. 1. In some examples, material 36 may include an electrically conductive or electrically semiconductive material, such as a ceramic. Example ceramics include boron carbide ($B_4C$), silicon carbide (SiC), alumina ($Al_2O_3$), composites thereof, or the like.

Electrical signal source 34 may include any device configured to output an electrical signal to electrodes 38. The electrical signal may include, for example, a DC signal. In some examples, electrical signal source 34 may output a current signal; in other examples, electrical signal source 34 may output a voltage signal. In some examples, electrical signal source 34 may be similar to or substantially the same as electrical signal source 14 of FIG. 1.

In the example shown in FIG. 3, each electrode of plurality of electrodes 38 is electrically coupled to material 36 using any suitable type of electrical connection, including, for example, an electrically conductive adhesive, an electrically conductive solder, embedding electrodes 38 in material 36, dielectrically coupled via capacitive coupling, or the like. Each electrode of plurality of electrodes 38 is electrically coupled to switch network 40 using a respective electrically conductive lead. In some examples, the plurality of electrodes 38 are distributed across a surface area of material 36, as shown in FIG. 3. In other examples, the plurality of electrodes 38 are distributed around a perimeter of material 36. In some examples, plurality of electrodes 38 may be referred to as a set of N electrodes 38.

In some examples, one or more electrodes may not be electrically coupled to material 36 and may be used as a reference electrode for single-ended voltage measurements between one electrode of plurality of electrodes 38 and the reference electrode. The reference electrode may be at a selected voltage, such a ground or an offset voltage. In some examples, the single-ended voltages may be used in the techniques described herein to determine whether material 36 (or material 16) includes a crack or other defect. In other examples, differential voltages between two electrodes electrically coupled to material 36 (or material 16) may be determined by comparing (e.g., subtracting) single ended voltages associated with the two electrodes, and these differential voltages may be used in the techniques described herein to determine whether material 36 (or material 16) includes a crack or other defect. For example, computing device 32 may determine a first single ended voltage between first electrode 38A and a reference electrode, computing device 32 may determine a second single ended voltage between second electrode 38B and the reference electrode, and computing device 32 may determine a differential voltage between first electrode 38A and second electrode 38B by subtracting the second single ended voltage from the first single ended voltage.

Switch network 40 includes a plurality of inputs and a plurality of outputs, with respective inputs electrically coupled to each respective output by the network of switches. For example, switch network 40 may include a pair of inputs electrically coupled to electrical signal source 34, and at least a pair of inputs electrically coupled to computing device 32. Switch network 40 may include at least as many outputs are there are electrodes 38. For example, in the example shown in FIG. 3, system 30 includes twelve electrodes, and switch network 40 thus includes at least twelve outputs. Each electrode of electrodes 38 is electrically coupled to a respective output of switch network 40.

Computing device 32 is configured to control operation of system 30, including electrical signal source 34 and switch network 40. Computing device 32 may include any of a wide range of devices, including computer servers, desktop computers, notebook (i.e., laptop) computers, tablet computers, and the like. In some examples, computing device 32 may include a processor. The processor may include one or more microprocessors, digital signal processors (DSP), application specific integrated circuits (ASIC), field programmable gate arrays (FPGA), or other digital logic circuitry. In some examples, computing device 32 may include an ADC or system 30 may include a separate ADC. In examples in which the ADC is separate from computing device 12, the ADC may be electrically coupled between switch network 40 and computing device 12. The ADC may measure the voltage across respective pairs of measurement electrodes.

Computing device 32 is communicatively coupled to electrical signal source 34 and electrically coupled to switch network 40, e.g., either directly or indirectly via an external device, such as an ADC. Computing device 32 may be configured to control electrical signal source 34 to output an electrical signal, and may be configured to control switch network 40 to connect a selected pair of electrodes 38 to electrical signal source 34 to serve as a pair of drive electrodes, such that the electrical signal output by electrical signal source 34 is output to the pair of drive electrodes.

Computing device 32 is also configured to cause switch network 40 to connect selected electrode of electrodes 38 to computing device with another electrode of electrodes 38 or a reference electrode not electrically coupled to material 36 to serve as a pair of measurement electrodes. In this way, computing device 32 may determine a voltage across material 36 in response to the electrical signal output by electrical signal source 34. Further details regarding an example technique performed by system 30 are described below with respect to FIG. 4.

Figure 4:
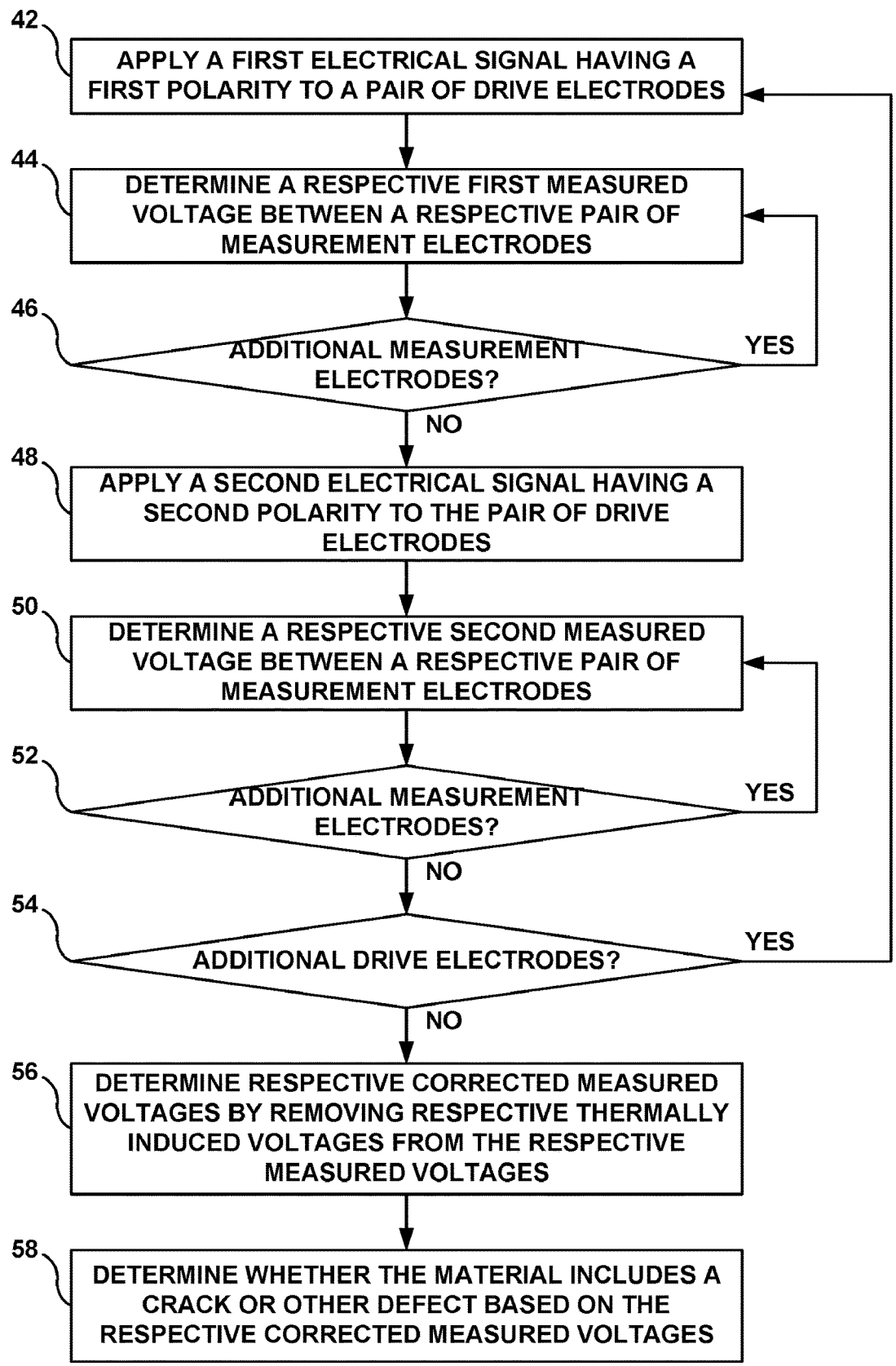
FIG. 4 is a flow diagram illustrating an example technique for determining whether a material includes a crack or other defect by measuring a voltage in the material and suppressing thermally induced voltage from the measured voltage.

FIG. 4 is flow diagram illustrating an example technique for determining presence of a crack or other defect in a material by measuring a voltage in the material and suppressing thermally induced voltage from the measured voltage. The technique of FIG. 4 will be described with reference to system 30 of FIG. 3 for clarity. However, it will be appreciated that the technique of FIG. 4 may be performed by other systems and computing devices, and that system 30 may be used to perform other techniques.

The technique of FIG. 4 includes applying a first electrical signal having a first polarity to a first pair of drive electrodes electrically coupled to material 36 (42). For example, computing device 32 may cause switch network 40 to electrically couple electrical signal source 34 to a selected pair of electrodes 38, which serves as the first pair of drive electrodes. The selected pair of electrodes 38 may include any two electrodes of electrodes 38. In some examples, the selected pair of electrodes 38 may be adjacent to each other; in other examples, the selected pair of electrodes may be spaced apart. For example, in some instances, the selected pair of electrodes 38 may be substantially opposite each other in the array of electrodes, e.g., electrode 38A and electrode 38L or electrode 38F and electrode 38G.

Computing device 32 then may cause electrical signal source 34 to apply the first electrical signal having the first polarity to the first pair of drive electrodes electrically coupled to material 36 (42), e.g., via switch network 40. The first electrical signal may include, for example, a DC signal, and may include a current signal or a voltage signal. In some examples, the type of electrical signal may depend on the composition of material 36. For example, a DC signal may be used to measure a voltage of an electrically conductive or electrically semiconductive material, while an AC signal may be used to measure a voltage of an electrically conductive material, an electrically semiconductive material, or a dielectric material. Computing device 32 also may control electrical signal source 34 to generate the first electrical signal with a selected amplitude, duration, frequency, and other signal characteristics.

The technique of FIG. 4 also includes, while applying the first electrical signal having the first polarity to the first pair of drive electrodes, determining a first measured voltage between a pair of measurement electrodes (44). For example, computing device 32 may cause switch network 40 to electrically couple computing device 32 to a selected pair of measurement electrodes. The selected pair of measurement electrodes may be any two electrodes from electrodes 38, or one electrode from electrodes 38 and a reference electrode not electrically coupled to material 36. Neither of the measurement electrodes is being used as one of the electrodes in the drive pair of electrodes. In some examples, the two electrodes in the pair of measurement electrodes may be adjacent to each other, e.g., electrode 38B and electrode 38C, or electrode 38D and electrode 38J. In other example, the two electrodes in the pair of measurement electrodes may be spaced each other with one or more electrodes between, e.g., electrode 38B and electrode 38D, or electrode 38E and electrode 38H. Using adjacent electrodes as the pair of measurement electrodes may result in a higher signal-noise-ratio in the voltage measurement, but may reduce an area of material 36 for which the voltage is measured.

Regardless of the particular electrodes coupled to computing device 32 as the pair of measurement electrodes, computing device 32 may determine a first measured voltage between the pair of measurement electrodes (44) while electrical signal source 34 is applying the first electrical signal having the first polarity to the selected pair of drive electrodes (42).

In some examples, computing device 32 may be configured to determine a respective first measured voltage for a plurality of pairs of measurement electrodes for each pair of drive electrodes. Hence, in some examples, the technique of FIG. 4 further includes determining whether there is an additional pair of measurement electrodes at which to determine a first measured voltage (46) for the selected pair of drive electrodes. In some examples, each pair of measurement electrodes is a unique pair of electrodes (e.g., for the purposes of this the electrode pair 38A, 38B is the same as the electrode pair 38B, 38A). In some examples, no two pairs of measurement electrodes share a common electrode. For example, a third, different electrode pair (a second pair of measurement electrodes) may not share any electrodes with a second, different electrode pair (a first pair of measurement electrodes). In other examples, different pairs of measurement electrodes may include one common electrode. For example, a third, different electrode pair (a second pair of measurement electrodes) may share exactly one electrode with the second, different electrode pair (a first pair of measurement electrodes).

In response to determining that there is an additional pair of electrodes to be used as a pair of measurement electrodes (the "YES" branch of decision block 46), computing device 32 may control switch network 40 to couple the selected additional pair of electrodes to computing device 32. Computing device 32 then may determine a first measured voltage between the selected additional pair of electrodes.

Computing device 32 may repeat this determination (46), coupling of selected pairs of measurement electrodes, and determination of a respective first measured voltage (44) until computing device 32 determines there are no more additional pairs of electrodes 38 to be used as a pair of measurement electrodes for the selected pair of drive electrodes and the first polarity (the "NO" branch of decision block 46).

Computing device 32 then may cause electrical signal source 34 to apply a second electrical signal having a second, opposite polarity to the first pair of drive electrodes electrically coupled to material 36 (48), e.g., via switch network 40. The second polarity of the second electrical signal is opposite the first polarity of the first electrical signal, i.e., in examples in which the first electrical signal has a positive polarity referenced to a first drive electrode, the second electrical signal has a negative polarity.

Computing device 32 may cause, while applying the second electrical signal having the second polarity to the first pair of drive electrodes, determining a second measured voltage between a pair of measurement electrodes (50). For example, computing device 32 may cause switch network 40 to electrically couple computing device 32 to a selected pair of measurement electrodes. The pair of measurement electrodes may be the same as a pair of measurement electrodes at which computing device 32 determined a first measurement voltage. The selected pair of measurement electrodes may be any two electrodes from electrodes 38, or one electrode from electrodes 38 and a reference electrode not electrically coupled to material 36.

Regardless of the particular electrodes coupled to computing device 32 as the pair of measurement electrodes, computing device 32 may determine a second measured voltage between the pair of measurement electrodes (50) while electrical signal source 34 is applying the second electrical signal having the second, opposite polarity to the selected pair of drive electrodes (48).

In some examples, computing device 32 may be configured to determine a respective second measured voltage for a plurality of pairs of measurement electrodes for each pair of drive electrodes. Hence, in some examples, the technique of FIG. 4 further includes determining whether there is an additional pair of measurement electrodes at which to determine a second measured voltage (52) for the selected pair of drive electrodes. In some examples, each pair of measurement electrodes is the same as a pair of measurement electrodes for which computing device 32 determined a first measured voltage.

In response to determining that there is an additional pair of electrodes to be used as a pair of measurement electrodes (the "YES" branch of decision block 52), computing device 32 may control switch network 40 to couple the selected additional pair of electrodes to computing device 32. Computing device 32 then may determine a second measured voltage between the selected additional pair of electrodes (50).

Computing device 32 may repeat this determination (52), coupling of selected pairs of measurement electrodes, and determination of a respective second measured voltage (50) until computing device 32 determines there are no more additional pairs of electrodes 38 to be used as a pair of measurement electrodes for the selected pair of drive electrodes and the first polarity (the "NO" branch of decision block 52).

Computing device 32 then may determine whether there is an additional pair of drive electrodes to apply the electrical signal to (54). For example, computing device 32 may be configured to utilize each unique pair of electrodes as a pair of drive electrodes.

Upon selecting a new pair of drive electrodes (the "YES" branch of decision block 54), computing device 32 may control switch network 40 to electrically couple the selected pair of drive electrodes to electrical signal source 34. Computing device 32 then may cause electrical signal source 34 to apply the first electrical signal to the new selected pair of drive electrodes (42). Computing device then may cause switch network 40 to electrically couple computing device 32 to a selected pair of measurement electrodes, and may determine a respective first measured voltage between the selected pair of measurement electrodes (44). Again, computing device 32 may determine whether there is an additional pair of measurement electrodes at which to measure a first measured voltage (46) for the selected pair of drive electrodes. In response to determining that there is an additional pair of electrodes to be used as a pair of measurement electrodes (the "YES" branch of decision block 46) for the selected pair of drive electrodes, computing device 32 may control switch network 40 to couple the selected additional pair of electrodes to computing device 32. Computing device 32 then may determine a measurement voltage across the selected additional pair of electrodes. Computing device 32 may repeat this determination (46), coupling of selected pairs of measurement electrodes, and determination of a respective first measured voltage (44) until computing device 32 determines there are no more additional pairs of electrodes 38 to be used as a pair of measurement electrodes for the selected pair of drive electrodes (the "NO" branch of decision block 46).

Computing device 32 then may cause electrical signal source 34 to apply a second electrical signal having a second, opposite polarity to the selected pair of drive electrodes electrically coupled to material 36 (48), e.g., via switch network 40. The second polarity of the second electrical signal is opposite the first polarity of the first electrical signal. Computing device 32 may cause, while applying the second electrical signal having the second polarity to the first pair of drive electrodes, determining a second measured voltage between a pair of measurement electrodes (50). For example, computing device 32 may cause switch network 40 to electrically couple computing device 32 to a selected pair of measurement electrodes. The pair of measurement electrodes may be the same as a pair of measurement electrodes at which computing device 32 determined a first measurement voltage. The selected pair of measurement electrodes may be any two electrodes from electrodes 38, or one electrode from electrodes 38 and a reference electrode not electrically coupled to material 36.

Regardless of the particular electrodes coupled to computing device 32 as the pair of measurement electrodes, computing device 32 may determine a second measured voltage between the pair of measurement electrodes (50) while electrical signal source 34 is applying the second electrical signal having the second, opposite polarity to the selected pair of drive electrodes (48). In some examples, computing device 32 may be configured to determine a respective second measured voltage for a plurality of pairs of measurement electrodes for each pair of drive electrodes. Hence, in some examples, the technique of FIG. 4 further includes determining whether there is an additional pair of measurement electrodes at which to determine a second measured voltage (52) for the selected pair of drive electrodes. In response to determining that there is an additional pair of electrodes to be used as a pair of measurement electrodes (the "YES" branch of decision block 52), computing device 32 may control switch network 40 to couple the selected additional pair of electrodes to computing device 32. Computing device 32 then may determine a second measured voltage between the selected additional pair of electrodes (50). Computing device 32 may repeat this determination (52), coupling of selected pairs of measurement electrodes, and determination of a respective second measured voltage (50) until computing device 32 determines there are no more additional pairs of electrodes 38 to be used as a pair of measurement electrodes for the selected pair of drive electrodes and the first polarity (the "NO" branch of decision block 52).

Computing device 32 then may determine whether there is an additional pair of electrodes 38 to be used as a pair of drive electrodes (48). Computing device 32 may repeat this algorithm until computing device 32 determines there are no more additional pairs of electrodes 38 to be used as a pair of drive electrodes (the "NO" branch of decision block 54).

Once computing device 32 has determined that there are no more additional pairs of electrodes 38 to be used as a pair of drive electrodes (the "NO" branch of decision block 48), computing device 32 may determine, for each respective pair of drive electrodes, respective corrected measured voltages for each respective pair of measurement electrodes by suppressing respective thermally induced voltages from the respective measured voltages (56). For example, for each pair of drive electrodes, computing device 32 determined a plurality of respective first measured voltages and a plurality of respective second measured voltages, one first measured voltage and one second measured voltage for each respective pair of measurement electrodes. For each respective pair of measurement electrodes, computing device 32 may suppress the respective thermally induced voltage by subtracting the respective second measured voltage from the respective first measured voltage, or vice versa. This results in a respective corrected measured voltage for each respective pair of measurement electrodes, for each respective pair of drive electrodes.

Computing device 32 then may utilize the respective corrected measured voltages to determine whether material 36 includes a crack or other defect (58). In some examples, similar to the technique of FIG. 2, computing device 32 may determine whether material 36 includes a crack or other defect based on a comparison between voltages. For example, computing device 32 or another computing device may perform steps (42)-(56) of the technique of FIG. 4 on material 36 at a first time at which it is known that material 36 is intact, i.e., does not include a crack or other defect. For example, the first time may be a time at which material 36 is manufactured, or a time at which an independent measurement (e.g., X-ray radiology or X-ray CT scan) may be used to verify that material 36 is intact, undamaged, or does not include a crack. These respective control voltages may be stored (e.g., in a memory device associated with computing device 32) for later use. For example, the respective control voltages may be stored in a data structure in which each respective control voltage is associated with a pair of drive electrodes to which the electrical signal was applied during the voltage measurement and a pair of measurement electrodes with which the respective control voltage was measured. In other examples, the control voltage may be determined using a model of material 36 in an intact (undamaged) state, or the control voltage may be determined as an average (e.g., mean) of a plurality of similar materials (e.g., in geometry and composition) that are known to be intact (undamaged).

Computing device 32 then may compare the respective corrected measured voltages to respective control voltages and determine whether material 36 includes the crack or other defect based on the comparison. For example, computing device 32 may compare each respective corrected measured voltage with a corresponding (i.e., associated with the same pair of drive electrodes and the same pair of measurement electrodes) control voltage. As an example, computing device 32 may subtract the corresponding control voltage from the respective measurement voltage. In some examples, computing device 32 may compare the respective voltage difference (between the respective corrected measured voltage and the respective control voltage) to a threshold voltage value.

The threshold voltage value may be selected so that a voltage difference above the threshold voltage value is meaningful (e.g., indicative of a crack or other defect) and a voltage difference below the threshold voltage value is not meaningful (e.g., is not indicative of a crack or other defect). In some examples, the threshold value may be selected to be a voltage value that is slightly greater than a noise floor of the measurement, such that any voltage difference that exceeds the noise floor is determined by computing device 32 to be indicative of a crack or other defect.

In some examples, after comparing each respective corrected measured voltage against a corresponding control voltage and comparing the difference to the threshold voltage value to determine if the respective corrected measured voltage is indicative of a crack or other defect, computing device 32 may determine whether a crack or other defect is present in material 36 based on the plurality of indications. For example, computing device 32 may determine a number of differences that are indicative of a crack and compare this number of differences to a threshold number of differences to determine if material 36 includes a crack or other defect.

In some examples, rather than utilizing differences between respective corrected measured voltages and respective control voltages or threshold voltage values directly, computing device 32 may calculate an approximate impedance distribution within material 36 to determine whether material 36 includes a crack or other defect (50). In some examples, reconstruction of the impedance distribution may be achieved by minimizing difference between the output of a physics-based simulation tool with the respective control voltages, and the respective measurement voltages. For example, computing device 32 may be programmed with a finite element model (FEM) of material 36 which implements the physics-based simulation. The FEM of material 36 may include substantially accurate (e.g., accurate or approximately accurate) geometry of material 16 (e.g., the shape and volume of material 36), and also may include substantially accurate (e.g., accurate or approximately accurate) locations of electrodes 38 attached to material 36. In some examples, the FEM of material 36 may additionally include representative properties of material 36, including, for example, conductivity, resistivity, other related electrical properties, and the like. The FEM of material 36 may include representative properties of material 36 for each respective node representing material 36.

Calculating the approximate impedance distribution to determine whether material 36 includes a crack of other defect is an ill-posed inverse problem, in which the outputs (the respective measurement voltages) are known but the properties of material 36 that produce the outputs are unknown. Moreover, more than one set of properties of material 36 may produce the outputs. Hence, computing device 32 may utilize a regularization technique to constrain the solution to solutions more likely to represent the properties of material 36 that would produce the respective measurement voltages.

In particular, computing device 32 may generate an objective function which combines outputs of the physics-based model, respective control voltages, the respective corrected measured voltages, and the regularization term. For example:

$$\arg\min_{x}\left\{\mathcal{F}(x) := \frac{1}{2}\|f(x) - y\|_{\ell_2}^2 + \lambda\frac{1}{2}\|Rx\|_{\ell_2}^2\right\}$$

where x is the approximate change in impedance distribution, f is an operator calculating the simulated difference in voltages based on input x utilizing the physics-based simulation, y is the measured difference in voltages, $l_2$ is a chosen norm, R is the regularization matrix, and X is the chosen weight of the regularization or regularization parameter. Computing device 32 may determine respective model control voltages based on the physics-based model and inputs representative of the electrical signal(s) applied to the respective pairs of drive electrodes. The respective model control voltages may be associated with respective pairs of measurement electrodes for each respective pair of drive electrodes used to collect the control voltages from material 36. Computing device 32 then may determine, using the physics-based model and inputs representative of the electrical signal(s) applied to the respective pairs of drive electrodes, respective model measurement voltages. The respective model measurement voltages may be associated with respective pairs of measurement electrodes for each respective pair of drive electrodes used to collect the measurement voltages from material 36. For each respective model measurement voltage, computing device 32 may determine a respective difference between the respective model measurement voltage and the respective model control voltage (f(x) in the equation above).

Computing device 32 also may determine a respective difference between the respective corrected measured voltage and the respective control voltage for each respective corrected measured voltage measured using material 36 to generate a set of actual voltage differences (y in the equation above).

Computing device 32 then may minimize the objective function by updating one or more parameters of the physics-based model. Computing device 32 may continue to iterate the model until a stopping criterion is reached. Computing device 32 then may determine the approximate change in impedance distribution that is representative of the condition of material 36. When iteration completes, the input to the model is the approximate change in impedance distribution.

Computing device 32 may then determine whether material 36 includes a crack or other defect based on the approximate change in impedance distribution. For example, computing device 32 may determine whether material 36 includes a crack or other defect based on the magnitude and location of the approximate impedance change within the material. In some examples, only the real portion of the impedance—the conductivity or resistivity—may be used by computing device 32 to determine whether material 36 includes a crack or other defect.

In some examples, rather than utilizing respective control voltages and respective model control voltages, computing device 32 may determine an approximate impedance distribution using an absolute form of the objective function, in which x is the impedance distribution, f is an operator calculating a set of the simulated voltages based on input x utilizing the physics-based simulation, y is a set of the corrected measured voltages, $l_2$ is a chosen norm, R is the regularization matrix, and X is the chosen weight of the regularization or regularization parameter.

Computing device 32 may output a representation of the determination of whether material 16 includes a crack or other defect. In some examples, the representation may include a simplified output, such as an indication of "Yes" or "No," "Crack" or "No Crack," "Damaged" or "Intact," or the like. The representation may be textual, icon-based, color-based, or the like. For example, the representation may include a green light to represent that material 16 is still intact or a red light to represent that material 16 is damaged or includes a crack or other defect.

As another example, computing device 32 may output a visual representation of the determination of whether material includes a crack or other defect. For example, in instances in which computing device 32 utilizes image reconstruction to determine the existence of a crack or other defect, computing device 32 may output a visual representation of material 16 and locations of the crack or other defect. For example, computing device 32 may output a false-color representation of conductivity or resistivity overlaid on a representation of material 16.

Figure 5:
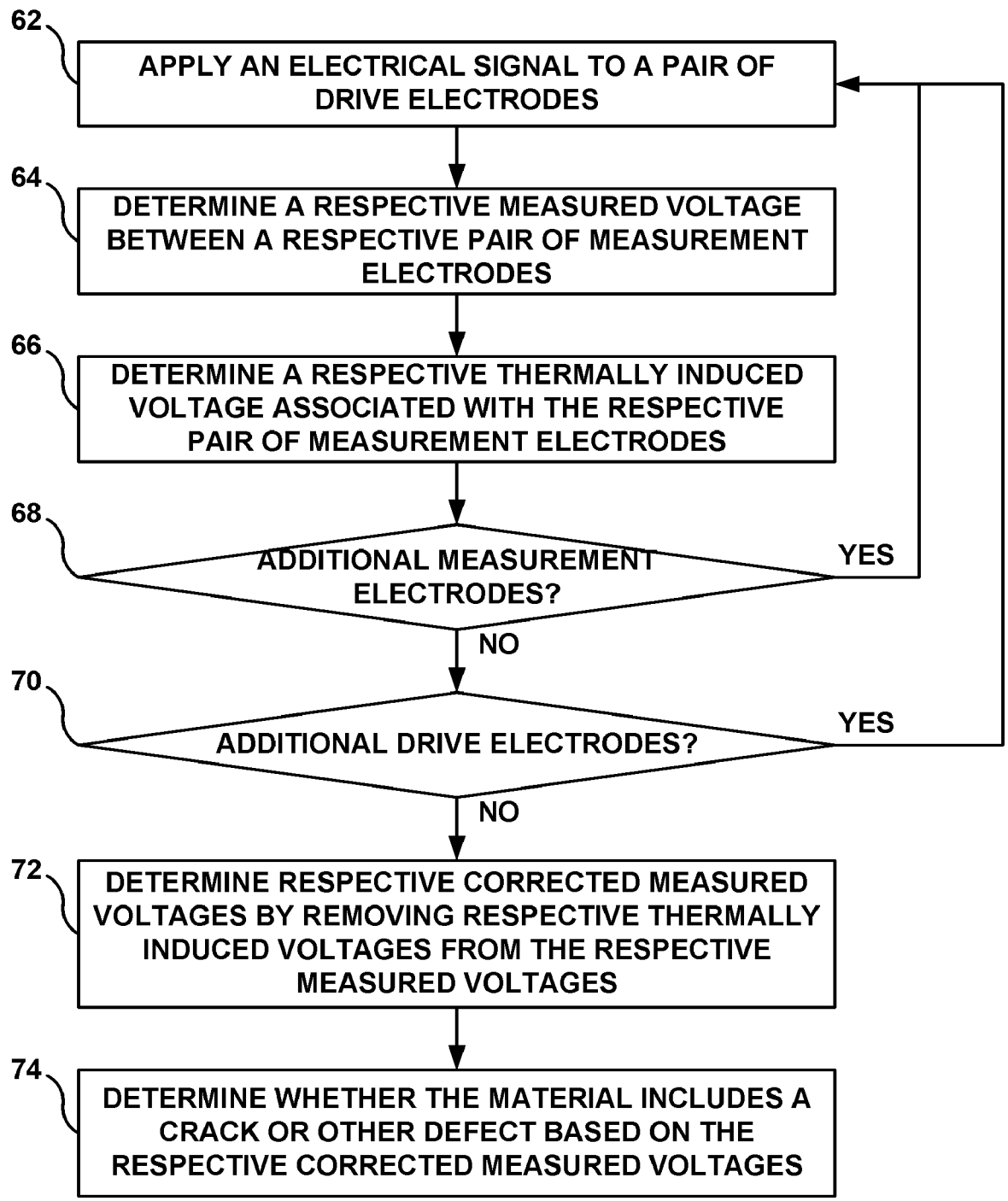
FIG. 5 is a flow diagram illustrating an example technique for determining whether a material includes a crack or other defect by measuring a voltage in the material and suppressing thermally induced voltage from the measured voltage.

FIG. 5 is flow diagram illustrating another example technique for determining presence of a crack or other defect in a material by measuring a voltage in the material and suppressing thermally induced voltage from the measured voltage. The technique of FIG. 5 will be described with reference to system 30 of FIG. 3 for clarity. However, it will be appreciated that the technique of FIG. 5 may be performed by other systems and computing devices, and that system 30 may be used to perform other techniques.

The technique of FIG. 5 includes applying an electrical signal to a first pair of drive electrodes electrically coupled to material 36 (62). Step (62) may be similar to or substantially the same as step (42) of FIG. 4.

The technique of FIG. 5 also includes, while applying the electrical signal to the first pair of drive electrodes, determining a measured voltage between a pair of measurement electrodes (64). For example, computing device 32 may cause switch network 40 to electrically couple computing device 32 to a selected pair of measurement electrodes. The selected pair of measurement electrodes may be any two electrodes from electrodes 38, or one electrode from electrodes 38 and a reference electrode not electrically coupled to material 36.

Regardless of the particular electrodes coupled to computing device 32 as the pair of measurement electrodes, computing device 32 may determine a measured voltage between the pair of measurement electrodes (64) while electrical signal source 34 is applying the electrical signal to the selected pair of drive electrodes (62).

Computing device 32 then may determine a thermally induced voltage associated with the respective pair of measurement electrodes (64). For example, computing device 12 may determine a voltage between the selected pair of measurement electrodes when electrical signal source 14 is not applying the electrical signal to the selected pair of drive electrodes and is not applying the electrical signal to the selected pair of measurement electrodes. Any voltage in material 36 detected between the selected pair of measurement electrodes when no electrical signal is being applied to material 36 may be thermally induced voltage, e.g., induced due to temperature gradients within material 36 between the location of the first measurement electrode and the location of the second measurement electrode.

In some examples, computing device 32 may be configured to determine a respective measured voltage and a respective thermally induced voltage for a plurality of respective pairs of measurement electrodes for each pair of drive electrodes. Hence, in some examples, the technique of FIG. 5 further includes determining whether there is an additional pair of measurement electrodes at which to determine a measured voltage (68) for the selected pair of drive electrodes. In response to determining that there is an additional pair of electrodes to be used as a pair of measurement electrodes (the "YES" branch of decision block 68), computing device 32 may control switch network 40 to couple the selected additional pair of electrodes to computing device 32. Computing device 32 then may determine a measured voltage between the selected additional pair of electrodes (64) and determine a respective thermally induced voltage associated with the respective pair of measurement electrodes (66).

Computing device 32 may repeat this determination (58), coupling of selected pairs of measurement electrodes, and determination of a respective measured voltage (64) and thermally induced voltage (66) until computing device 32 determines there are no more additional pairs of electrodes 38 to be used as a pair of measurement electrodes for the selected pair of drive electrodes and the first polarity (the "NO" branch of decision block 68).

Computing device 32 then may determine whether there is an additional pair of drive electrodes to apply the electrical signal to (70). For example, computing device 32 may be configured to utilize each unique pair of electrodes as a pair of drive electrodes. Upon selecting a new pair of drive electrodes (the "YES" branch of decision block 70), computing device 32 may control switch network 40 to electrically couple the selected pair of drive electrodes to electrical signal source 34. Computing device 32 then may cause electrical signal source 34 to apply the electrical signal to the new selected pair of drive electrodes (62). Computing device then may cause switch network 40 to electrically couple computing device 32 to a selected pair of measurement electrodes, and may determine a respective measured voltage between the selected pair of measurement electrodes (64). Computing device 32 also may determine a respective thermally induced voltage associated with the respective pair of measurement electrodes (66). Again, computing device 32 may determine whether there is an additional pair of measurement electrodes at which to measure a measured voltage (64) for the selected pair of drive electrodes. In response to determining that there is an additional pair of electrodes to be used as a pair of measurement electrodes (the "YES" branch of decision block 68) for the selected pair of drive electrodes, computing device 32 may control switch network 40 to couple the selected additional pair of electrodes to computing device 32. Computing device 32 then may determine a measured voltage for the selected additional pair of electrodes (64) and determine a respective thermally induced voltage associated with the respective pair of measurement electrodes (66). Computing device 32 may repeat this determination (68), coupling of selected pairs of measurement electrodes, and determination of a respective measured voltage (64) and a respective thermally induced voltage (66) until computing device 32 determines there are no more additional pairs of electrodes 38 to be used as a pair of measurement electrodes for the selected pair of drive electrodes (the "NO" branch of decision block 68).

Computing device 32 then may determine whether there is an additional pair of electrodes 38 to be used as a pair of drive electrodes (70). Computing device 32 may repeat this algorithm until computing device 32 determines there are no more additional pairs of electrodes 38 to be used as a pair of drive electrodes (the "NO" branch of decision block 70).

Once computing device 32 has determined that there are no more additional pairs of electrodes 38 to be used as a pair of drive electrodes (the "NO" branch of decision block 48), computing device 32 may determine, for each respective pair of drive electrodes, respective corrected measured voltages for each respective pair of measurement electrodes by suppressing respective thermally induced voltages from the respective measured voltages (72). For example, for each pair of measurement electrodes, for each pair of drive electrodes, computing device may subtract the respective thermally induced voltage associated with the respective pair of measurement electrodes (for the respective pair of drive electrodes) from the respective measured voltage associated with the respective pair of measurement electrodes (for the respective pair of drive electrodes). The result may be a set of corrected measured voltages associated with respective pairs of measurement electrodes, for each respective pair of drive electrodes.

Computing device 32 then may utilize the respective corrected measured voltages to determine whether material 36 includes a crack or other defect (74). In some examples, similar to the technique of FIG. 5, computing device 32 may determine whether material 36 includes a crack or other defect based on a comparison between voltages, as described above with reference to FIGS. 2 and 4. In some examples, rather than utilizing differences between respective corrected measured voltages and respective control voltages or threshold voltage values directly, computing device 32 may calculate an approximate impedance distribution within material 36 to determine whether material 36 includes a crack or other defect (74), as described above with respect to FIG. 4.

Computing device 32 may output a representation of the determination of whether material 16 includes a crack or other defect. In some examples, the representation may include a simplified output, such as an indication of "Yes" or "No," "Crack" or "No Crack," "Damaged" or "Intact," or the like. The representation may be textual, icon-based, color-based, or the like. For example, the representation may include a green light to represent that material 36 is still intact or a red light to represent that material 36 is damaged or includes a crack or other defect.

As another example, computing device 32 may output a visual representation of the determination of whether material includes a crack or other defect. For example, in instances in which computing device 32 utilizes image reconstruction to determine the existence of a crack or other defect, computing device 32 may output a visual representation of material 36 and locations of the crack or other defect. For example, computing device 32 may output a false-color representation of conductivity or resistivity overlaid on a representation of material 36.

In this way, computing device 32 may determine corrected measured voltages by suppressing thermally induced voltage from measured voltages, alone or in combination with a four-point voltage measurement, which may offer improved accuracy and sensitivity for detecting cracks or other defects in material 36 compared to a two-point voltage measurement and not suppressing thermally induced voltages. Additionally, a four-point voltage measurement system 30 may offer improved portability and cost compared to an X-ray radiography or X-ray computed tomography system, while offering sufficient accuracy and detail to enable detection of cracks or other defects in material 36 while material 36 is being used in the field.

The techniques described in this disclosure may be implemented, at least in part, in hardware, software, firmware, or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various techniques described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Computer readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable media. In some examples, an article of manufacture may include one or more computer-readable storage media.

In some examples, a computer-readable storage medium may include a non-transitory medium. The term "non-transitory" may indicate that the storage medium is not embodied in a carrier wave or a propagated signal. In certain examples, a non-transitory storage medium may store data that can, over time, change (e.g., in RAM or cache).

Clause 1: A method comprising: applying an electrical signal to a first electrode pair electrically coupled to the material; while applying the electrical signal to the first electrode pair, determining a measured voltage between a second, different electrode pair, wherein at least one electrode of the second, different electrode pair is electrically coupled to the material; determining a corrected measured voltage by suppressing a thermally induced voltage from the measured voltage; and determining whether the material includes a crack or other defect based on the corrected measured voltage.

Clause 2: The method of clause 1, wherein determining the corrected measured voltage by suppressing the thermally induced voltage from the measured voltage comprises: measuring the thermally induced voltage using the second, different electrode pair when no electrical signal is applied to the first electrode pair or the second electrode pair; and subtracting the thermally induced voltage from the measured voltage.

Clause 3: The method of clause 1, wherein: applying an electrical signal to a first electrode pair electrically coupled to the material comprises applying a first electrical signal having a first polarity to the first electrode pair electrically coupled to the material; while applying the electrical signal to the first electrode pair, determining the measured voltage between the second, different electrode pair electrically coupled to the material comprises, while applying the first electrical signal to the first electrode pair, determining a first measured voltage between the second, different electrode pair electrically coupled to the material; the method further comprises: applying a second electrical signal having a second, substantially equal magnitude, opposite polarity to the first electrode pair electrically coupled to the material; while applying the second electrical signal to the first electrode pair, determining a second measured voltage between the second, different electrode pair electrically coupled to the material; an determining the corrected measured voltage by suppressing the thermally induced voltage from the measured voltage comprises subtracting the first measured voltage from the second measured voltage to reduce an effect of the thermally induced voltage and determine the corrected measured voltage.

Clause 4: The method of clause 3, wherein determining the corrected measured voltage by suppressing the thermally induced voltage from the measured voltage further comprises dividing the result of subtracting the first measured voltage from the second measured voltage by two to determine the corrected measured voltage.

Clause 5: The method of any one of claims 1 to 4, wherein the electrical signal is a DC voltage signal or a DC current signal.

Clause 6: The method of any one of clauses 1 to 5, wherein determining whether the material includes the crack or other defect based on the voltage comprises determining whether the material includes the crack or other defect by at comparing the corrected measured voltage to a reference voltage.

Clause 7: The method of any one of clauses 1 to 6, wherein both electrodes of the second, different electrode pair are electrically coupled to the material.

Clause 8: The method of any one of clauses 1 to 7, wherein a first electrode of the second, different electrode pair is electrically coupled to the material and a second electrode of the second, different electrode pair is electrically coupled to a common reference point.

Clause 9: A method comprising: for each respective pair of drive electrodes of a plurality of respective pairs of drive electrodes electrically coupled to the material, applying an electrical signal to the respective pair of drive electrodes; for each respective pair of drive electrodes, determining a respective measured voltage between each respective pair of measurement electrodes of a plurality of pairs of measurement electrodes while applying the electrical signal to the respective pair of drive electrodes, wherein at least one electrode of each respective pair of measurement electrodes is electrically coupled to the material; determining a respective corrected measured voltage for each respective pair of measurement electrodes by suppressing a respective thermally induced voltage from the respective measured voltage; and determining whether the material includes a crack or other defect based on the respective corrected measured voltages.

Clause 10: The method of clause 9, wherein determining the respective corrected measured voltage for each respective pair of measurement electrodes by suppressing the respective thermally induced voltage from the respective measured voltage comprises: measuring the respective thermally induced voltage using each respective pair of measurement electrodes when no electrical signal is applied to the respective pair of drive electrodes or the respective pair of measurement electrodes; and subtracting the respective thermally induced voltage associated with the respective pair of measurement electrodes from the respective measured voltage associated with the respective pair of measurement electrodes.

Clause 11: The method of clause 9, wherein: applying the electrical signal to the respective pair of drive electrodes comprises applying a first electrical signal having a first polarity to the respective pair of drive electrodes; determining the respective measured voltage between each respective pair of measurement electrodes of the plurality of pairs of measurement electrodes while applying the electrical signal to the respective pair of drive electrodes comprises determining a respective first measured voltage between each respective pair of measurement electrodes of a plurality of pairs of measurement electrodes while applying the first electrical signal having the first polarity to the respective pair of drive electrodes; the method further comprises: for each respective pair of drive electrodes of the plurality of respective pairs of drive electrodes electrically coupled to the material, applying a second electrical signal having a second, opposite polarity to the respective pair of drive electrodes; for each respective pair of drive electrodes, determining a respective second measured voltage between each respective pair of measurement electrodes of the plurality of pairs of measurement electrodes while applying the second electrical signal to the respective pair of drive electrodes; and determining the respective corrected measured voltage for each respective pair of measurement electrodes by suppressing the respective thermally induced voltage from the respective measured voltage comprises subtracting the respective first measured voltage associated with the respective pair of measurement electrodes from the respective second measured voltage to reduce an effect of the respective thermally induced voltage and determine the respective corrected measured voltage.

Clause 12: The method of clause 11, wherein determining the respective corrected measured voltage for each respective pair of measurement electrodes by suppressing the respective thermally induced voltage from the respective measured voltage further comprises dividing the result of subtracting the respective first measured voltage from the respective second measured voltage by two to determine the respective corrected measured voltage.

Clause 13: The method of any one of clauses 9 to 12, wherein the electrical signal is a DC voltage signal or a DC current signal.

Clause 14: The method of any one of clauses 9 to 13, wherein determining whether the material includes the crack or other defect based on the respective corrected measured voltages comprises determining whether the material includes the crack or other defect by at least comparing the respective corrected measured voltages to respective reference voltages.

Clause 15: The method of any one of clauses 9 to 14, wherein determining whether the material includes the crack or other defect based on the respective corrected measured voltages comprises: calculating an approximate change in impedance distribution within the material based on a physics-based simulation, inputs representative of the electrical signal(s) applied to the respective pairs of drive electrodes, the respective corrected measured voltages, and respective reference voltages; and determining that the material includes the crack or other defect based on the approximate change in impedance distribution.

Clause 16: The method of any one of clauses 9 to 14, wherein determining whether the material includes the crack or other defect based on the respective corrected measured voltages comprises:

calculating an approximate impedance distribution within the material based on a physics-based simulation, inputs representative of the electrical signal(s) applied to the respective pairs of drive electrodes, and the respective corrected measured voltages; and determining that the material includes the crack or other defect based on the approximate impedance distribution.

Clause 17: The method of any one of clauses 9 to 16, wherein a plurality of electrodes are distributed across a surface area of the material, and wherein the plurality of electrodes include the plurality of respective pair of drive electrodes and the at least one measurement electrode of each respective pair of measurement electrodes.

Clause 18: The method of any one of clauses 9 to 16, wherein a plurality of electrodes are distributed around a perimeter of the material, and wherein the plurality of electrodes include the plurality of respective drive electrode pairs and the at least one measurement electrode of each respective pair of measurement electrodes.

Clause 19: A system comprising: a set of N electrodes electrically coupled to a material; an electrical signal source; and a computing device configured to: cause the electrical signal source to apply an electrical signal to a first electrode pair from the set of N electrodes; while electrical signal source is applying the electrical signal to the first electrode pair, determine a measured voltage between a second, different electrode pair, wherein at least one electrode of the second, different electrode pair is from the set of N electrodes; determine a corrected measured voltage by suppressing a thermally induced voltage from the measured voltage; and determine whether the material includes a crack or other defect based on the corrected measured voltage Clause 20: The system of clause 19, wherein the computing device is configured to determine the corrected measured voltage by suppressing the thermally induced voltage from the measured voltage by at least: measuring the thermally induced voltage using the second, different electrode pair when no electrical signal is applied to the first electrode pair or the second, different electrode pair; and subtracting the thermally induced voltage from the measured voltage.

Clause 21: The system of clause 19, wherein the computing device is configured to: cause the electrical signal source to apply a first electrical signal having a first polarity to the first electrode pair; while the electrical signal source is applying the first electrical signal to the first electrode pair, determine a first measured voltage between the second, different electrode pair; cause the electrical signal source to apply a second electrical signal having a second, opposite polarity to the first electrode pair; while the electrical signal source is applying the second electrical signal to the first electrode pair, determine a second measured voltage between the second, different electrode pair; and determine the corrected measured voltage by at least subtracting the first measured voltage from the second measured voltage to reduce an effect of the thermally induced voltage and determine the corrected measured voltage.

Clause 22: The system of clause 21, wherein the computing device is further configured to determine the corrected measured voltage by at least dividing the result of subtracting the first measured voltage from the second measured voltage by two to determine the corrected measured voltage.

Clause 23: The system of any one of clauses 19 to 22, wherein the electrical signal is a DC voltage signal or a DC current signal.

Clause 24: The system of any one of clauses 19 to 23, wherein the computing device is configured to determine whether the material includes the crack or other defect by at least comparing the corrected measured voltage to a reference voltage.

Clause 25: The system of any one of clauses 19 to 24, wherein the set of N electrodes are distributed across a surface area of the material.

Clause 26: The system of any one of clauses 19 to 24, wherein the set of N electrodes are distributed are distributed around a perimeter of the material.

Clause 27: The system of any one of clauses 19 to 26, wherein the computing device is configured to: for each respective pair of drive electrodes of a plurality of respective pairs of drive electrodes electrically coupled to the material, cause the electrical signal source to apply an electrical signal to the respective pair of drive electrodes, wherein each respective pair of drive electrodes is from the set of N electrodes; for each respective pair of drive electrodes, determine a respective measured voltage between each respective pair of measurement electrodes of a plurality of pairs of measurement electrodes while the electrical signal source is applying the electrical signal to the respective pair of drive electrodes, wherein at least one measurement electrode of each respective pair of measurement electrodes is from the set of N electrodes; determine a respective corrected measured voltage for each respective pair of measurement electrodes by suppressing a respective thermally induced voltage from the respective measured voltage; determine whether the material includes the crack or other defect based on the respective corrected measured voltages.

Clause 28: The system of clause 27, wherein the computing device is configured to determine the respective corrected measured voltage for each respective pair of measurement electrodes by suppressing the respective thermally induced voltage from the respective measured voltage by at least: measuring the respective thermally induced voltage using each respective pair of measurement electrodes when no electrical signal is applied to the respective pair of drive electrodes or the respective pair of measurement electrodes; and subtracting the respective thermally induced voltage associated with the respective pair of measurement electrodes from the respective measured voltage associated with the respective pair of measurement electrodes.

Clause 29: The system of clause 27, wherein the computing device is configured to: cause the electrical signal source to apply a first electrical signal to the respective pair of drive electrodes; determine a respective first measured voltage between each respective pair of measurement electrodes of a plurality of pairs of measurement electrodes while the electrical signal source is applying the first electrical signal having the first polarity to the respective pair of drive electrodes; for each respective pair of drive electrodes of the plurality of respective pairs of drive electrodes electrically coupled to the material, cause the electrical signal source to apply a second electrical signal having a second, opposite polarity to the respective pair of drive electrodes; for each respective pair of drive electrodes, determine a respective second measured voltage between each respective pair of measurement electrodes of the plurality of pairs of measurement electrodes while the electrical signal source is applying the second electrical signal to the respective pair of drive electrodes; and determine the respective corrected measured voltage for each respective pair of measurement electrodes by at least subtracting the respective first measured voltage associated with the respective pair of measurement electrodes from the respective second measured voltage to reduce an effect of the respective thermally induced voltage and determine the respective corrected measured voltage.

Clause 30: The system of clause 29, wherein the computing device is further configured to determine the respective corrected measured voltage for each respective pair of measurement electrodes by at least dividing the result of subtracting the respective first measured voltage from the respective second measured voltage by two to determine the respective corrected measured voltage.

Clause 31: The system of any one of clauses 27 to 30, wherein the computing device is configured to determine whether the material includes the crack or other defect based on the respective corrected measured voltages by at least: calculating an approximate change in impedance distribution within the material based on a physics-based simulation, inputs representative of the electrical signal(s) applied to the respective pairs of drive electrodes, the respective corrected measured voltages, and respective reference voltages; and determining whether the material includes the crack or other defect based on the change in impedance distribution.

Clause 32: The system of any one of clauses 27 to 30, wherein the computing device is configured to determine whether the material includes the crack or other defect based on the respective voltages by at least: calculating an approximate impedance distribution within the material based on a physics-based simulation, inputs representative of the electrical signal(s) applied to the respective pairs of drive electrodes, and the respective corrected measured voltages; and determining whether the material includes the crack or other defect based on the approximate impedance distribution.

EXAMPLES

Example 1

A sensor system including twelve electrodes was assembled onto a ceramic plate around the perimeter of the ceramic plate. Electrical contact between the electrodes and the ceramic plate was made via a silver-loaded conductive epoxy available from Epo-Tek (Epoxy Technology, Inc., 14 Fortune Drive, Billerica, Mass. 01821. A current source was connected to a matrix to route to any of the 12 electrodes. Current was then routed to a pair of drive electrodes (a force electrode and a return electrode). Since the electrodes were in a 'ring' around the ceramic plate, all counting was modulo-n. For example, the set of 3-apart electrodes with n=12 is: (0,3), (1,4), (2,5), (3,6), (4,7), (5,8), (6,9), (7,10), (8,11), (9,0), (10,1), and (11,2). For each pair of drive electrodes, voltages were measured on adjacent electrodes that were not force or return. For example, if the pair of drive electrodes was (0,3), the measured pairs were (1,2), (4,5), (5,6), (6,7), (7,8), (8,9), (9,10), and (10,11). Voltages were measured on adjacent pairs (differential) for all pairs of drive electrodes 3, 4, 5, and 6 apart. Voltages were represented as Analog to Digital Converter (ADC) codes, which are unitless.

When the plates are relatively hotter, they will be more conductive, so the measured voltage is expected to change. For this example, a percentage difference was calculated for each voltage measurement, defined as:

$$\text{Percent Change}=(ADC\_cold-ADC\_hot)/ADC\_cold*100$$

Ideally this percent change was uniform across all measurements.

A metric defined as the standard deviation of the Percent Change is used to evaluate measurement methods.

Example 2

The steps in Example 1 were modified. For each of the measurement pair:

1. A current was passed from force to return electrode of a pair of drive electrodes.
2. A voltage was measured on an adjacent pair of measurement electrodes, defined as $V_{m1}$.
3. The current was reversed, by changing the output of the matrix, such that the force electrode becomes the return, and the return becomes the force electrode.
4. The voltage is measured a second time, using the same polarity as step 2, defined as $V_{m2}$.
5. The final corrected, measured voltage was then defined as $V_m=(V_{m1}-V_{m2})/2$.

This final corrected, measured voltage was then used in the analysis.

This technique works because the thermally induced voltage polarity depends on the temperature gradient. The voltage induced by the drive current depends on the applied polarity of the current. Thus by changing the polarity of the current the desired signal moves in the opposite direction as the thermally induced voltage and the error can be subtracted out. Analogously the thermally induced voltage could be calculated by $V_{error}=(V_{m1}+V_{m2})/2$.

Example 3

The reciprocal of Example 2 would be to keep the current polarity the same and then swap the polarity of the measurement electrodes. This did not cancel the thermoelectric error voltage, and in fact made the situation worse.

Table 1 below summarizes the results of Examples 1-3. Three plates were assembled and tested according to the methods of Examples 1-3. A complete dataset was 336 measurements under each test condition. Though the mean Percent Change is similar for all test methods, there was a benefit to using the method of Example 2. The standard deviation is much tighter, which means all measurements are closer to the mean, and look less like outliers. This reduces the 'noise' seen measuring plates at high temperature and will reduce false positive detection rates.

TABLE 1

| Plate No. | Example 1 | | Example 3 | | Example 2 | |
|---|---|---|---|---|---|---|
| | Mean % Change | Std Dev | Mean % Change | Std Dev | Mean % Change | Std Dev |
| 1 | 44.12 | 14.00 | 44.82 | 28.07 | 46.12 | 1.46 |
| 2 | 46.10 | 17.51 | 45.52 | 31.71 | 45.72 | 1.77 |
| 3 | 46.18 | 13.46 | 45.72 | 32.08 | 44.66 | 1.65 |

Various examples have been described. These and other examples are within the scope of the following claims.

What is claimed is:

1. A method comprising:
applying an electrical signal to a first electrode pair electrically coupled to a tested material;
while applying the electrical signal to the first electrode pair, determining a measured voltage between respective electrodes of a second, different electrode pair, wherein at least one respective electrode of the respective electrodes of the second, different electrode pair is electrically coupled to the tested material;
determining a corrected measured voltage by suppressing a thermally induced voltage from the measured voltage, wherein the thermally induced voltage is indicative of a thermoelectric effect of a temperature of the tested material; and
determining, based on the corrected measured voltage, that the tested material includes a defect.

2. The method of claim 1, wherein determining the corrected measured voltage by suppressing the thermally induced voltage from the measured voltage comprises subtracting the thermally induced voltage from the measured voltage.

3. The method of claim 1, wherein the electrical signal is a first electrical signal, wherein the measured voltage is a first measured voltage between the respective electrodes of the second, different electrode pair electrically coupled to the tested material, the method further comprising:
applying, to the first electrode pair electrically coupled to the tested material, a second electrical signal having a second magnitude that is substantially equal to a first magnitude of the first electrical signal and having a second polarity that is opposite to a first polarity of the first electrical signal; and
while applying the second electrical signal to the first electrode pair, determining a second measured voltage between the respective electrodes of the second, different electrode pair electrically coupled to the tested material,
wherein determining the corrected measured voltage by suppressing the thermally induced voltage from the measured voltage comprises subtracting the first measured voltage from the second measured voltage to reduce an effect of the thermally induced voltage with respect to determining the corrected voltage.

4. The method of claim 3, wherein determining the corrected measured voltage by suppressing the thermally induced voltage from the measured voltage further comprises dividing a result of subtracting the first measured voltage from the second measured voltage by two.

5. The method of claim 1, wherein the electrical signal is a DC voltage signal.

6. The method of claim 1, wherein the electrical signal is a DC current signal.

7. The method of claim 1, wherein determining that the tested material includes the defect based on the corrected measured voltage comprises determining that the defect by comparing the corrected measured voltage to a reference voltage.

8. The method of claim 1, wherein a first electrode of the second, different electrode pair is electrically coupled to the tested material and a second electrode of the second, different electrode pair is electrically coupled to a common reference point.

9. The method of claim 1, wherein the defect comprises a crack in the tested material.

10. The method of claim 1, further comprising determining, at a time when the electrical signal is not being applied to the first electrode pair, the thermally induced voltage using the second, different electrode pair.

11. An apparatus comprising:
means for applying an electrical signal to a first electrode pair electrically coupled to a tested material;
means for determining a measured voltage between respective electrodes of a second, different electrode pair while the electrical signal is applied to the first electrode pair, wherein at least one respective electrode of the respective electrodes of the second, different electrode pair is electrically coupled to the tested material;
means for determining a corrected measured voltage by suppressing a thermally induced voltage from the measured voltage, wherein the thermally induced voltage is indicative of a thermoelectric effect of a temperature of the tested material; and
means for determining, based on the corrected measured voltage, that the tested material includes a defect.

12. The apparatus of claim 11, wherein the defect comprises a crack in the tested material.

13. A system comprising:
a first electrode pair electrically coupled to a tested material;
a second, different electrode pair electrically coupled to the tested material; and
a computing device configured to:
apply an electrical signal to the first electrode pair;
determine a measured voltage between respective electrodes of a second, different electrode pair while applying the electrical signal to the first electrode pair, wherein at least one respective electrode of the respective electrodes of the second, different electrode pair is electrically coupled to the tested material;
determine a corrected measured voltage by suppressing a thermally induced voltage from the measured voltage, wherein the thermally induced voltage is indicative of a thermoelectric effect of a temperature of the tested material; and
determine, based on the corrected measured voltage, that the tested material includes a defect.

14. The system of claim 13, wherein the defect comprises a crack in the tested material.

15. The system of claim 13, wherein the control module is further configured to determine, at a time when the electrical signal is not being applied to the first electrode pair, the thermally induced voltage using the second, different electrode pair.

* * * * *